United States Patent
Morikawa et al.

(10) Patent No.: US 9,241,226 B2
(45) Date of Patent: *Jan. 19, 2016

(54) UNCOMFORTABLENESS THRESHOLD VALUE ESTIMATION SYSTEM AND METHOD, AND A PROGRAM THEREOF; HEARING AID ADJUSTMENT SYSTEM; AND UNCOMFORTABLENESS THRESHOLD VALUE PROCESSING CIRCUIT

(71) Applicant: Panasonic Corporation, Osaka (JP)

(72) Inventors: Koji Morikawa, Kyoto (JP); Shinobu Adachi, Nara (JP); Yumiko Kato, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 134 days.

This patent is subject to a terminal disclaimer.

(21) Appl. No.: 13/909,421

(22) Filed: Jun. 4, 2013

(65) Prior Publication Data

US 2013/0266163 A1    Oct. 10, 2013

Related U.S. Application Data

(63) Continuation of application No. PCT/JP2012/004245, filed on Jun. 29, 2012.

(30) Foreign Application Priority Data

Jun. 30, 2011  (JP) ................. 2011-146092

(51) Int. Cl.
| | |
|---|---|
| *H04R 25/00* | (2006.01) |
| *A61B 5/00* | (2006.01) |
| *A61B 5/0484* | (2006.01) |
| *A61B 5/12* | (2006.01) |
| *H04R 9/00* | (2006.01) |
| *H04R 23/00* | (2006.01) |

(52) U.S. Cl.
CPC ............ *H04R 25/70* (2013.01); *A61B 5/04845* (2013.01); *A61B 5/125* (2013.01); *A61B 5/6803* (2013.01); *A61B 5/6815* (2013.01); *H04R 9/00* (2013.01); *H04R 23/00* (2013.01); *H04R 25/00* (2013.01); *H04R 25/30* (2013.01)

(58) Field of Classification Search
CPC .......... H04R 25/00; H04R 9/00; H04R 23/00; H04R 25/70; H04R 25/30; A61B 5/6803; A61B 5/6815; A61B 5/04845; A61B 5/125
USPC ........................................ 381/60, 312; 607/55
See application file for complete search history.

(56) References Cited

U.S. PATENT DOCUMENTS

2001/0049480 A1* 12/2001 John et al. ............... 600/559
2004/0064066 A1    4/2004 John et al.

(Continued)

FOREIGN PATENT DOCUMENTS

| JP | 2004-179965 A | 6/2004 |
| JP | 2009-288354 A | 12/2009 |
| WO | WO 01/87147 A2 | 11/2001 |
| WO | WO 2008/038650 A1 | 4/2008 |

OTHER PUBLICATIONS

International Search Report for corresponding International Application No. PCT/JP2012/004245 mailed Sep. 11, 2012.
Kimitsuki et al., "Inner ear auditory testing in patients with normal hearing showing hyperacusis", Audiology Japan 52, pp. 152-156, 2009 and concise explanation (cited in [0011] of the specification).
Thornton et al., "The objective estimation of loudness discomfort level using auditory brainstem evoked responses", MRC Institute of Hearing Research, England, 1987 (cited in [0012] of the specification).

(Continued)

*Primary Examiner* — Matthew Eason
*Assistant Examiner* — Sean H Nguyen
(74) *Attorney, Agent, or Firm* — Renner, Otto, Boisselle & Sklar, LLP

(57) ABSTRACT

An exemplary UCL estimation system including: an output section configured to present to a user a first sound, and a second sound after lapse of a first predetermined time from a point of presenting the first sound, the first sound having a sound pressure within a predetermined sound pressure range, and the second sound having a same sound pressure as that of the first sound; a measurement section configured to measure an electroencephalogram signal of the user; an extraction section configured to extract, from an electroencephalogram signal measured within a second predetermined time from a point of presenting the second sound, a characteristic amount of an event-related potential of the signal; and an estimation section configured to estimate, by referring to a predetermined relationship between characteristic amount values of event-related potential and uncomfortableness threshold values, an uncomfortableness threshold value corresponding to the extracted characteristic amount of the potential.

16 Claims, 19 Drawing Sheets

(56) References Cited

U.S. PATENT DOCUMENTS

| | | |
|---|---|---|
| 2004/0204659 A1 | 10/2004 | John et al. |
| 2006/0036297 A1* | 2/2006 | Seidman ............... A61N 1/361 607/55 |
| 2009/0163828 A1* | 6/2009 | Turner et al. .................. 600/559 |
| 2012/0283593 A1* | 11/2012 | Searchfield et al. .......... 600/559 |

OTHER PUBLICATIONS

Jishoukanrendeni (ERP) Manyuaru-P300 WO Chushinni—(or "Event-Related Potential (ERP) Manual-mainly concerning P300—"), edited by Kimitaka Kaga et al., Shinohara Shuppan Shinsha, 1995, p. 30 and concise explanation (cited in [0086] of the specification).

Co-pending U.S. Appl. No. 13/788,806, filed Mar. 7, 2013.

* cited by examiner

| BEFORE ELECTROENCEPHALOGRAM EXPERIMENT (AVERAGE) | 91.2dB |
|---|---|
| AFTER ELECTROENCEPHALOGRAM EXPERIMENT (AVERAGE) | 94.0dB |
| OVERALL AVERAGE | 92.6dB |
| AMOUNT OF FLUCTUATION BEFORE AND AFTER EXPERIMENT | 3.75 ± 3.89dB |

(12 TEST SUBJECTS)

UPPER VIEW          FRONTAL VIEW

FIG.4A
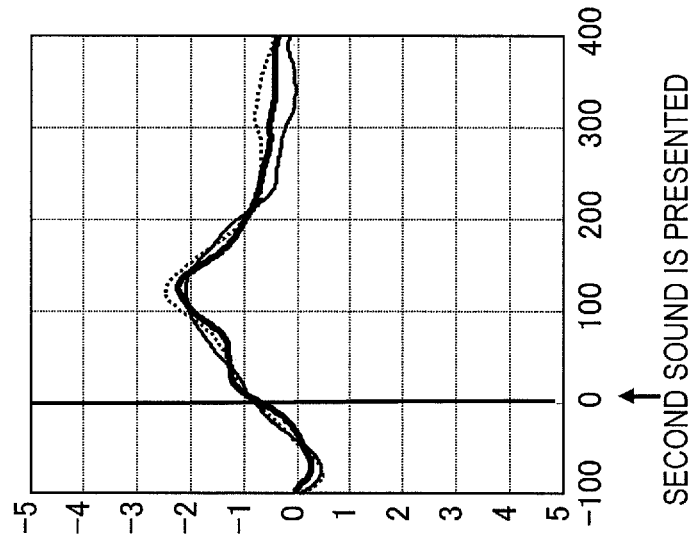
(a) ERP AFTER FIRST SOUND PRESENTATION
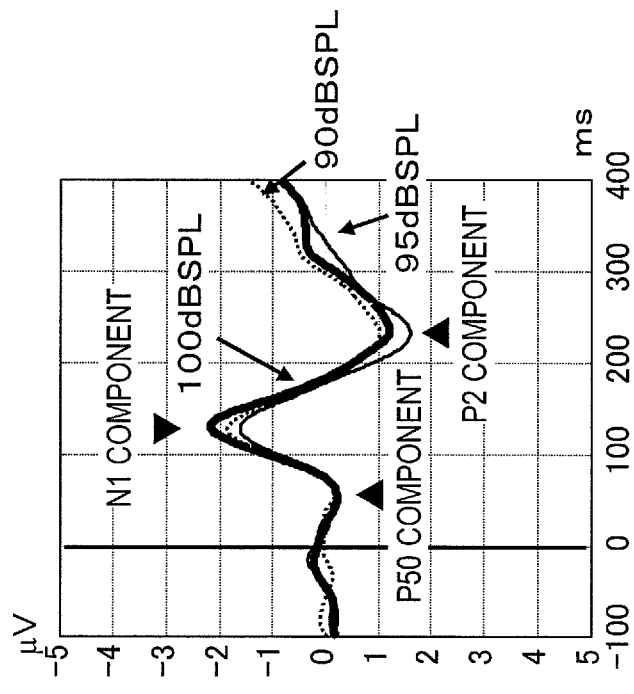
(b) ERP AFTER SECOND SOUND PRESENTATION FIG.4B
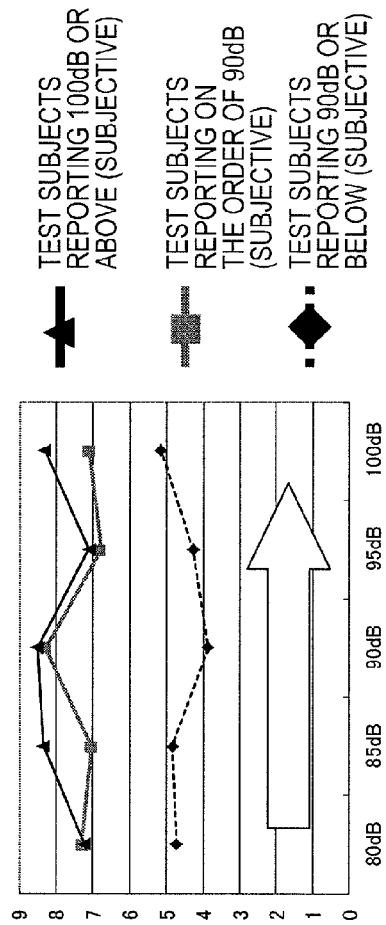
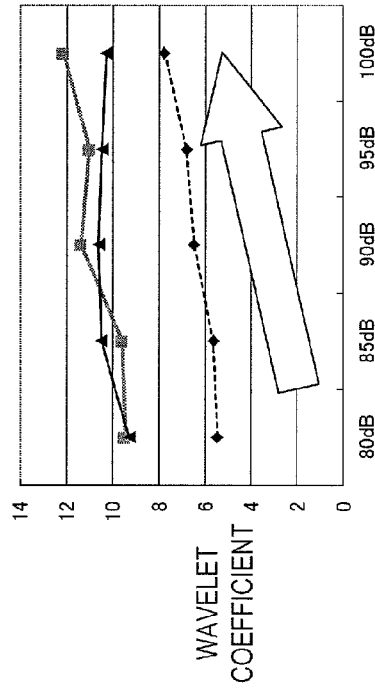
(a) ERP AFTER FIRST SOUND PRESENTATION
(b) ERP AFTER SECOND SOUND PRESENTATION

| TESTED EAR | FREQUENCY (Hz) | SOUND PRESSURE (dB) | | | | |
|---|---|---|---|---|---|---|
| | | 70 | 75 | 80 | 85 | 90 |
| RIGHT | 1000 | 0 | 1 | 0 | 1 | 1 |
| | 2000 | 1 | 1 | 0 | 0 | 1 |
| | 4000 | 1 | 0 | 1 | 1 | 0 |
| LEFT | 1000 | 0 | 0 | 1 | 1 | 0 |
| | 2000 | 1 | 0 | 1 | 0 | 1 |
| | 4000 | 1 | 1 | 0 | 1 | 1 |

(NUMBER OF PRESENTATIONS)

| TESTED EAR | FREQUENCY (Hz) | UNCOMFORTABLENESS THRESHOLD VALUE (dB) |
|---|---|---|
| RIGHT | 1000 | 80 |
| | 2000 | 95 |
| | 4000 | 90 |
| LEFT | 1000 | 95 |
| | 2000 | 100 |
| | 4000 | 85 |

FIG.17A

| WAVELET COEFFICIENT FOR SECOND SOUND (MEAN VALUE AT PRESENTATION SOUND PRESSURES: 80, 85, and 90dB) | UCL ESTIMATION VALUE |
|---|---|
| ~4.0 | 85dB |
| 4.0~6.0 | 90dB |
| 6.0~8.0 | 95dB |
| 8.0~8.5 | 100dB |
| 8.5~ | 105dB |

FIG.17C

| N1-P2 AMPLITUDE FOR SECOND SOUND (MEAN VALUE AT PRESENTATION SOUND PRESSURES: 80, 85, and 90dB) | UCL ESTIMATION VALUE |
|---|---|
| ~1.25 | 85dB |
| 1.25~1.5 | 90dB |
| 1.5~2.0 | 95dB |
| 2.0~2.5 | 100dB |
| 2.5~ | 105dB |

FIG.17D

| TESTED EAR | UNCOMFORTABLENESS THRESHOLD VALUE (dB) |
|---|---|
| RIGHT | 90 |
| LEFT | 93 |

UNCOMFORTABLENESS THRESHOLD VALUE ESTIMATION SYSTEM AND METHOD, AND A PROGRAM THEREOF; HEARING AID ADJUSTMENT SYSTEM; AND UNCOMFORTABLENESS THRESHOLD VALUE PROCESSING CIRCUIT

This is a continuation of International Application No. PCT/JP2012/004245, with an international filing date of Jun. 29, 2012, which claims priority of Japanese Patent Application No. 2011-146092, filed on Jun. 30, 2011, the contents of which are hereby incorporated by reference.

BACKGROUND

1. Technical Field

The present disclosure relates to a technique of assessing whether a speech sound has been comfortably heard or not. More specifically, the present disclosure relates to a device, method, program, and the like for estimating an uncomfortableness threshold value for a pure tone or a speech sound, for the "fitting" of a hearing aid or the like to provide a sound of appropriate loudness for each individual user by adjusting the amount of amplification of external sounds with respect to each frequency.

2. Description of the Related Art

In recent years, people suffering from presbycusis are increasing in number due to the aging society. Due to the increased opportunities for listening to loud music for long hours as well as other influences, there is an increasing number of young people suffering from hypacusia associated with acoustic traumas. Moreover, due to the downsizing and improved performance of hearing aids, users have come to wear hearing aids with less of a psychological barrier. This has led to an increasing number of users wearing hearing aids.

A user suffering from hypacusia has difficulty in hearing sounds of a specific frequency(s). This specific frequency varies from user to user. A hearing aid amplifies the amplitude of a sound signal at this specific frequency, thus making it easier for the user to hear sounds.

A hearing aid is required to change the amount by which it amplifies sounds, in accordance with the level of deterioration in the hearing of the user. Therefore, before beginning use of a hearing aid, "fitting" is required for adjusting the amount of sound amplification in accordance with the hearing of each user.

The purpose of fitting is to keep the output sound pressure of a hearing aid at an MCL (most comfortable level). As used herein, the "output sound pressure" of a hearing aid refers to the fluctuations in air pressure that are perceivable to humans as a sound. The MCL defines a sound pressure which guarantees comfortable hearing by the user. The hearing aid needs to ensure that the output sound pressure satisfies MCL for each sound frequency.

Examples of inappropriate fitting may be: (1) an insufficient amount of amplification for sound pressure; or (2) an excessive amount of amplification for sound pressure. For example, if the amount of amplification for sound pressure is insufficient, the user cannot aurally distinguish audios. In this case, the aforementioned purpose of using a hearing aid is not met. If the amount of amplification for sound pressure is excessive, the user is capable of aural distinction of audios, but may find the audio to be loud, which prevents the user from using the hearing aid over a long time. Therefore, a fitting of a hearing aid needs to be done in such a manner that neither (1) nor (2) occurs. Especially (2) possesses a possibility that the hearing aid may present an audio with an unduly high sound pressure to the user. This has created danger of hurting the user's ear with audios having high sound pressure.

Fitting generally comes into two steps. A first step of fitting is measuring an audiogram. An "audiogram" refers to a measurement of a threshold value (hearing threshold level: HTL) defining the smallest sound pressure of a pure tone that allows it to be heard by a user. An audiogram may be, for example, a diagram in which such a threshold value (decibel value) is plotted for different frequencies (e.g., 250 Hz, 500 Hz, 1000 Hz, 2000 Hz, 4000 Hz).

A second step of fitting is determining an amount of amplification for sound pressure. For example, by using a mathematical function (called a fitting theory) for estimating an amount of sound amplification, an amount of amplification is determined for each frequency and for each sound pressure of an input sound. There are a number of types of fitting theories, for example: the half-gain method, in which an insertion gain of each frequency is made half of the threshold value of that frequency; Berger's method, which slightly augments the amplify from 1000 Hz to 4000 Hz by taking into consideration the frequency band and level of conversational voices; the POGO method which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level.

Moreover, the "fitting theory" is also inclusive of a method of determining an amount of amplification for sound pressure by utilizing the information of a threshold value, a UCL (uncomfortable level) which is a high sound pressure level that is felt uncomfortable to the user, and the MCL. In that case, before determining an amount of amplification for sound pressure, the UCL and MCL are either measured or estimated. In order to avoid problem (2) above, it is necessary to measure the UCL, and set an amount of amplification in a range such that the UCL is not exceeded.

Similarly to audiogram measurement, a UCL is to be measured for each frequency. Conventionally, the UCL is measured based on subjective reporting. "Subjective reporting" involves, after a user hears a sound, the user making a subjective account as to how the sound was felt to him or her. For example, while using an audiometer, continuous sounds or discontinuous sounds are presented to the user by using an ascending method (i.e., the sound pressure level is gradually increased), and the user is asked to report whether the sound pressure is so loud that he or she cannot tolerate hearing it for a long time. Then, a sound pressure beyond which the user cannot retain tolerance over a long time, according to their own reporting, is defined as a UCL (Takashi KIMITSUKI et al., "Inner ear auditory testing in patients with normal hearing showing hyperacusis", 2009; hereinafter "Non-Patent Document 1").

A UCL measurement through subjective reporting is difficult because the UCL criterion will fluctuate under individual influences or the influences of linguistic expressions, and thus there is no established technique. Therefore, methods of taking an objectively measurement of UCL by using electroencephalogram are under development. For example, in a technique disclosed in Thornton, A. R. et al., "The objective estimation of loudness discomfort level using auditory brainstem evoked responses", Scandinavian Audiology, Vol. 16, No. 4, P. 219-225, 1987 (hereinafter "Non-Patent Document 2"), a UCL is estimated based on a relationship between the stimulation intensity and the latency of a V wave that is contained in a brainstem response called ABR (auditory brainstem response). As the sound pressure increases, the V wave latency decreases. The sound pressure of the sound which the user was hearing when the decrease in V wave latency became saturated is identified. A sound pressure which is obtained by adding a constant (e.g., 15 or 10) to this identified sound pressure is defined as the UCL.

On the other hand, generally speaking, an MCL (most comfortable level) is difficult to be measured through subjective reporting, and therefore is often approximated as a gradient (half gain) which is a half of the hearing threshold value or a median between the UCL and the hearing threshold value.

Thus, in order to measure a UCL, it is necessary to actually present a loud sound to the user before the UCL can be calculated based on the user's reply, or a brain stem response, e.g., ABR.

SUMMARY

One non-limiting, and exemplary embodiment provides a technique of estimating a UCL of a user without allowing the user to hear an overbearing sound which is felt uncomfortable.

In one general aspect, an uncomfortableness threshold value estimation system as one implementation of the present invention includes: an output section configured to present to a user a first sound, and to present to the user a second sound after lapse of a first predetermined time from a point of presenting the first sound, the first sound having a sound pressure within a predetermined sound pressure range, and the second sound having a same sound pressure as that of the first sound; a biological signal measurement section configured to measure an electroencephalogram signal of the user; an extraction section configured to extract, from an electroencephalogram signal which is measured within a second predetermined time from a point of presenting the second sound, a characteristic amount of an event-related potential of the electroencephalogram signal; and an estimation section configured to estimate, by referring to a predetermined relationship between characteristic amount values of event-related potential and uncomfortableness threshold values, an uncomfortableness threshold value corresponding to the extracted characteristic amount of the event-related potential.

With an uncomfortableness threshold value estimation system as one implementation of the present invention, a UCL which is needed for the adjustment of a hearing aid can be estimated without forcing a user to hear an overbearing sound which is felt uncomfortable, thus reducing the burden of a user in a hearing aid adjustment.

The embodiment above can be implemented as a system, a method, or a computer program, or implemented by using a combination of a system, a method, and/or a computer program.

BRIEF DESCRIPTION OF THE DRAWINGS

FIG. 1A diagram showing UCL evaluation results measured through subjective reporting.

FIG. 4A includes: (a), which is a graph showing three kinds of total arithmetic mean waveforms obtained based on an event-related potential after presenting a first sound; and (b), which is a graph showing three kinds of total arithmetic mean waveforms obtained based on an event-related potential after presenting a second sound.

FIG. 4B includes (a) and (b) showing results 21 and 22, respectively, of plotting characteristic amount changes in response to different sound pressures at presentation.

FIG. 17A is a diagram showing an exemplary data structure of a reference DB 7.

FIG. 17C is a diagram showing an example of a reference DB 7 in the case of using N1P2 amplitude as a characteristic amount.

FIG. 17D is a diagram showing an exemplary output format of uncomfortableness threshold values in the case where speech sounds are employed.

DETAILED DESCRIPTION

Figures 1, 2:
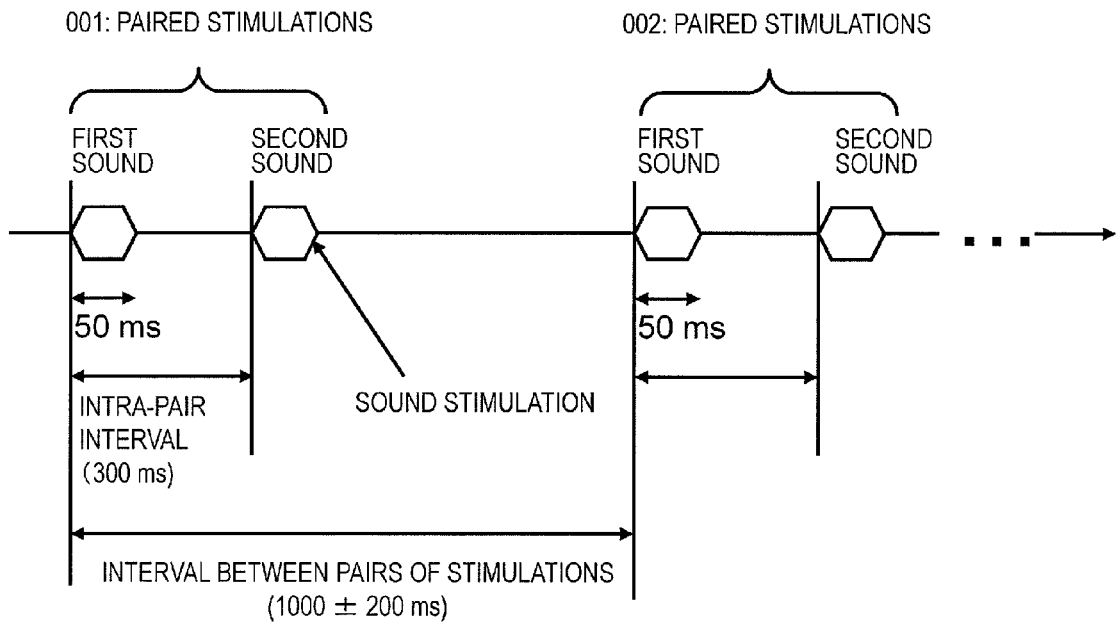
FIG. 2 A diagram outlining the protocol of an electroencephalogram measurement experiment.

The above-described constructions disclosed in Non-Patent Document 1 and Non-Patent Document 2 both adopt a method where a sound stimulation is presented to the user at an uncomfortable sound pressure level, thus placing the user in an uncomfortable state, and only then a UCL determination is made. This represents a problem in making a hearing assessment that an overbearing sound is presented to the user, and that the user must actually experience an uncomfortable state. This is due to the conventional techniques' approach of examining an uncomfortableness threshold value based on the user being in an uncomfortable state.

Conventional techniques of UCL estimation which utilize an electroencephalogram oblige the user to hear an overbearing sound which is felt uncomfortable, thus being not preferable to the user. In order to solve this problem, the inventors has made the present disclosure.

The following is an outline of an implementation(s) of the present disclosure.

An uncomfortableness threshold value estimation system as one implementation of the present invention includes: an output section configured to present to a user a first sound, and to present to the user a second sound after lapse of a first predetermined time from a point of presenting the first sound, the first sound having a sound pressure within a predetermined sound pressure range, and the second sound having a same sound pressure as that of the first sound; a biological signal measurement section configured to measure an electroencephalogram signal of the user; an extraction section configured to extract, from an electroencephalogram signal which is measured within a second predetermined time from a point of presenting the second sound, a characteristic amount of an event-related potential of the electroencephalogram signal; and an estimation section configured to estimate, by referring to a predetermined relationship between characteristic amount values of event-related potential and uncomfortableness threshold values, an uncomfortableness threshold value corresponding to the extracted characteristic amount of the event-related potential.

In one embodiment, the uncomfortableness threshold value estimation system further includes a presentation sound control section configured to determine the predetermined sound pressure range according to a predetermined criterion, and to control the first sound and the second sound so as to be presented from the output section at a sound pressure which is equal to or less than an upper limit of the sound pressure range.

In one embodiment, under control of the presentation sound control section, the output section outputs the first sound and the second sound at a predetermined frequency and sound pressure.

In one embodiment, under control of the presentation sound control section, the output section, presents a speech sound in a predetermined sound pressure range as the first sound and the second sound.

In one embodiment, under control of the presentation sound control section, the output section presents the second sound after 100 milliseconds or more have elapsed from the point of presenting the first sound.

In one embodiment, the output section outputs at least two pairs of sound stimulations, where each pair of sound stimulations is defined by a first sound and a second sound; and the presentation sound control section changes the sound pressure from sound stimulation to sound stimulation.

In one embodiment, the output section outputs a first pair of sound stimulations and a second pair of sound stimulations, where each pair of sound stimulations is defined by a first sound and a second sound; and the presentation sound control section controls the sound stimulations so that the first pair of sound stimulations is presented and then the second pair of sound stimulations is presented within a range of 1000 ms±200 ms therefrom.

In one embodiment, the extraction section extracts a wavelet coefficient concerning time and frequency as the characteristic amount, by applying a wavelet transform to the electroencephalogram signal which is measured within the second predetermined time from the point of presenting the second sound.

In one embodiment, by referring to a reference database defining a relationship between wavelet coefficients and uncomfortableness threshold values, the estimation section estimates an uncomfortableness threshold value corresponding to the wavelet coefficient obtained as the characteristic amount.

In one embodiment, the second predetermined time is a period in which an N1 component and a P2 component of the event-related potential in response to the second sound are observable; and the extraction section extracts an N1P2 amplitude as the characteristic amount, the N1P2 amplitude being an absolute value of a difference between a peak potential of the N1 component and a peak potential of the P2 component.

In one embodiment, by referring to a reference database defining a relationship between N1P2 amplitudes and uncomfortableness threshold values, the estimation section estimates an uncomfortableness threshold value corresponding to the N1P2 amplitude obtained as the characteristic amount.

A hearing aid adjustment system as another implementation of the present invention includes: a hearing aid; an uncomfortableness threshold value estimation system of any of the aforementioned embodiments; and a setting section configured to receive the uncomfortableness threshold value estimated by the uncomfortableness threshold value estimation system and setting the uncomfortableness threshold value to the hearing aid as a maximum output value.

An uncomfortableness threshold value processing circuit as still another implementation of the present invention receives an electroencephalogram signal of a user measured by a biological signal measurement section, and causes an output section to present a sound stimulation, the uncomfortableness threshold value processing circuit including: a presentation sound control section configured to cause the output section to present a first sound, and to present a second sound after lapse of a first predetermined time from a point of presenting the first sound, the first sound having a sound pressure within a predetermined sound pressure range, and the second sound having the sound pressure; an extraction section configured to extract, from an electroencephalogram signal which is measured within a second predetermined time from a point of presenting the second sound, a characteristic amount of an event-related potential of the electroencephalogram signal; and an estimation section configured to estimate, by referring to a predetermined relationship between characteristic amount values of event-related potential and uncomfortableness threshold values, an uncomfortableness threshold value corresponding to the extracted characteristic amount of the event-related potential.

An uncomfortableness threshold value estimation method as still another implementation of the present invention includes the steps of: presenting to a user a first sound and presenting to the user a second sound after lapse of a first predetermined time from a point of presenting the first sound, the first sound having a sound pressure within a predetermined sound pressure range, and the second sound having a same sound pressure as that of the first sound; measuring an electroencephalogram signal of the user; from an electroencephalogram signal which is measured within a second predetermined time from a point of presenting the second sound, extracting a characteristic amount of an event-related potential of the electroencephalogram signal; and by referring to a predetermined relationship between characteristic amount values of event-related potential and uncomfortableness threshold values, estimating an uncomfortableness threshold value corresponding to the extracted characteristic amount of the event-related potential.

A computer program as still another implementation of the present invention is stored on a non-transitory computer-readable medium, and to be executed by a computer provided in an uncomfortableness threshold value processing circuit of an uncomfortableness threshold value estimation system, the computer program causing the computer to execute the steps of: presenting to a user a first sound and presenting to the user a second sound after lapse of a first predetermined time from a point of presenting the first sound, the first sound having a sound pressure within a predetermined sound pressure range, and the second sound having a same sound pressure as that of the first sound; acquiring an electroencephalogram signal of the user; from an electroencephalogram signal which is measured within a second predetermined time from a point of presenting the second sound, extracting a characteristic amount of an event-related potential of the electroencephalogram signal; and by referring to a predetermined relationship between characteristic amount values of event-related potential and uncomfortableness threshold values, estimating an uncomfortableness threshold value corresponding to the extracted characteristic amount of the event-related potential.

An uncomfortableness threshold value estimation system as still another implementation of the present invention includes: a sound pressure range determination section configured to determine a sound pressure range in which to present sounds to a user; a first sound presentation section and a second sound presentation section configured to determine first and second sounds to be presented at a predetermined time interval, the first and second sounds being of a same sound pressure and frequency, the sound pressure being in the sound pressure range determined by the sound pressure range determination section; a sound stimulation output section configured to output the first and second sounds as sound stimulations; a biological signal measurement section configured to measure an electroencephalogram of the user; an event-related potential acquisition/accumulation section configured to acquire, from the electroencephalogram measured by the biological signal measurement section, an event-related potential based on a timing of outputting the second sound as a starting point, and to accumulate the event-related potential together with attributes of the second sound presented, the attributes being the sound pressure, the frequency, and a tested ear; a reference database retaining a criterion for estimating an uncomfortableness threshold value from a characteristic amount of the event-related potential; and an uncomfortableness threshold value estimation section configured to process data accumulated in the event-related potential acquisition/accumulation section in accordance with the criterion retained in the reference database, and to estimate an uncomfortableness threshold value, the uncomfortableness threshold value exceeding the sound pressure range determined by the sound pressure range determination section.

In one embodiment, the criterion retained in the reference database is a criterion for an uncomfortableness threshold value concerning an event-related potential in response to the second sound.

In one embodiment, the criterion retained in the reference database is an amplitude amount based on an N1 component and a P2 component in response to the second sound, such that a larger uncomfortableness threshold value is estimated for a larger value of the amplitude amount.

In one embodiment, the reference database employs a wavelet coefficient as a characteristic amount for the second sound, such that a larger uncomfortableness threshold value is estimated for a larger value of the wavelet coefficient.

In one embodiment, the sound pressure range determination section adopt presentation sound pressures of 80 dB, 85 dB, and 90 dB irrespective of the user.

In one embodiment, the sound pressure range determination section sets a value which is lower by a predetermined value than an uncomfortableness threshold value estimated based on a fitting theory from a hearing threshold level of the user.

In one embodiment, the sound pressure range determined by the sound pressure range determination section is a range of sound pressures which are greater than a sound pressure of a hearing threshold level of the user but are smaller than an expected uncomfortableness threshold value of the user.

In one embodiment, an upper limit value of the sound pressure range determined by the sound pressure range determination section is an uncomfortableness threshold value estimated from the hearing threshold level of the user.

In one embodiment, the event-related potential acquisition/accumulation section acquires not only the event-related potential based on the timing of outputting the second sound but also an event-related potential based on a timing of outputting the first sound, and accumulates each event-related potential together with attributes of the sound stimulation presented, the attributes being the sound pressure, the frequency, and a tested ear.

An uncomfortableness threshold value estimation method as still another implementation of the present invention includes: a sound pressure range determination step of determining a sound pressure range in which to present sounds to a user; a first sound presentation step and a second sound presentation step of determining first and second sounds to be presented at a predetermined time interval, the first and second sounds being of a same sound pressure and frequency, the sound pressure being in the sound pressure range determined in the sound pressure range determination step; a sound stimulation output step of outputting the first and second sounds as sound stimulations; a biological signal measurement step of measuring an electroencephalogram of the user; an event-related potential acquisition/accumulation step of acquiring, from the electroencephalogram measured in the biological signal measurement step, an event-related potential based on a timing of outputting the second sound as a starting point, and accumulating the event-related potential together with attributes of the second sound presented, the attributes being the sound pressure, the frequency, and a tested ear; and an uncomfortableness threshold value estimation step of processing data accumulated in the event-related potential acquisition/accumulation step in accordance with a criterion retained in a reference database for estimating an uncomfortableness threshold value from a characteristic amount of the event-related potential, and estimating an uncomfortableness threshold value, the uncomfortableness threshold value exceeding the sound pressure range determined in the sound pressure range determination step.

A computer program as still another implementation of the present invention is stored on a non-transitory computer-readable medium, and to be executed by a computer provided in an uncomfortableness threshold value estimation system, the computer program causing the computer provided in the uncomfortableness threshold value estimation system to execute: a sound pressure range determination step of determining a sound pressure range in which to present sounds to a user; a first sound presentation step and a second sound presentation step of determining first and second sounds to be presented at a predetermined time interval, the first and second sounds being of a same sound pressure and frequency, the sound pressure being in the sound pressure range determined in the sound pressure range determination step; a sound stimulation output step of outputting the first and second sounds as sound stimulations; a biological signal measurement step of measuring an electroencephalogram of the user; an event-related potential acquisition/accumulation step of acquiring, from the electroencephalogram measured in the biological signal measurement step, an event-related potential based on a timing of outputting the second sound as a starting point, and accumulating the event-related potential together with attributes of the second sound presented, the attributes being the sound pressure, the frequency, and a tested ear; and an uncomfortableness threshold value estimation step of processing data accumulated in the event-related potential acquisition/accumulation step in accordance with a criterion retained in a reference database for estimating an uncomfortableness threshold value from a characteristic amount of the event-related potential, and estimating an uncomfortableness threshold value, the uncomfortableness threshold value exceeding the sound pressure range determined in the sound pressure range determination step.

Prior to description of an illustrative embodiment of the present disclosure, the terminology used in the present specification and experiments which were conducted by the inventors will be described, followed by findings which the inventors have obtained from results of the experiments. Thereafter, the present embodiment will be described.

First, the definitions of the terms used in the present specification will be described.

An "event-related potential (ERP)" is a fluctuation in the potential of an electroencephalogram (EEG) that occurs in response to a stimulation.

A "sound stimulation" is a stimulation, in the form of a sound, which is presented to a user.

An "N1 component" is the potential of a negative component which is contained in an electroencephalogram up to about 100 ms since the point of presenting a sound stimulation. An N1 component is included in the event-related potential.

A "P2 component" is the potential of a positive component which is contained in an electroencephalogram at about 200 ms since the point of presenting a sound stimulation. A P2 component is included in the event-related potential.

"Latency" means a length of time, from the point of presenting a sound stimulation as a starting point, until a peak potential of a positive component or negative component appears.

A "negative component" generally refers to a potential which is smaller than 0 µV.

A "positive component" generally refers to a potential which is greater than 0 µV. However, when a comparison is to be made between potentials, the potential that has a greater value in the minus direction may be regarded as a negative component. Similarly, when a comparison is to be made between potentials, the potential that has a greater value in the positive direction may be regarded as a positive component.

An "uncomfortableness threshold value (uncomfortable loudness level: UCL)" defines a sound pressure which is so loud as to make the user feel uncomfortable.

A "hearing threshold level (hearing threshold level: HTL)" defines the smallest sound pressure of a sound that allows it to be heard by a user.

A "pure tone" is a sound which repetitively undergoes periodic oscillation at one frequency, expressed as a sine wave.

According to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)", there are 30 to 50 ms of differences (shifts) in event-related potential waveform between individuals, generally speaking. Therefore, in the present specification, the terms "about X ms" and "near X ms" are inclusive of a range of 30 to 50 ms before or after X ms, e.g., 100 ms±30 ms being meant for X=100, and 200 ms±50 ms being meant for X=200, and so on. A 50 ms shift, which provides for a broader range, may well be assumed in order to allow for individual differences; in this case, "about X ms" would mean no less than (X−50) and no more than (X+50) ms.

Hereinafter, with reference to the attached drawings, each illustrative embodiment of the uncomfortableness threshold value estimation system according to the present disclosure will be described.

An uncomfortableness threshold value estimation system according to an illustrative embodiment of the present disclosure makes it possible to estimate an uncomfortableness threshold value by presenting a sound ("presentation sound") having a sound pressure of a loudness not felt uncomfortable to the user. Prior to description of the estimation technique, experiments conducted by the inventors and the experimental results thereof will be described. Thereafter, characteristics of an induced electroencephalographic response which enables UCL estimation, which the inventors have found from experimental data, will be described.

(Explanation of Experimental Outline)

1. Experimental Outline

The inventors have conducted the following two experiments to collect some fundamental data for the estimation of an uncomfortableness threshold value with respect to a pure tone, aiming to realize an uncomfortableness threshold value estimation for enabling objective measurement of a UCL in a short time and with a high precision.

One is a subjective report experiment where UCL was measured based on subjective reporting. One subjective report experiment each was conducted before and after an electroencephalogram measurement experiment (see below). The UCL data obtained from this subjective report experiment was used as reference data, i.e., a hallmark for estimation based on electroencephalogram.

Another is an electroencephalogram measurement experiment where responses to sound stimulations were measured. As sound stimulations, two pure tones of the same frequency and the same sound pressure level were presented with a predetermined interval therebetween. Hereinafter, such two presented sound stimulations of pure tones may be referred to as "paired stimulations" or "a pair of stimulations". Event-related potentials in response to these presented sound stimulations were acquired as experimental data for UCL value estimation.

Considering the experimental results, the inventors have realized the feasibility of a distinguisher which is capable of estimating a UCL value, even when presenting paired stimulations of a sound pressure lower than a sound pressure which would generally be deemed as the UCL, from a characteristic amount in the electroencephalogram components (event-related potential) to the first sound and the second sound.

According to this technique, a UCL estimation is possible in a short time and with a high precision, without presenting any overbearing sound so loud as to make the user feel uncomfortable.

Hereinafter, experiments conducted by the inventors, and electroencephalographic traits which have been elucidated by analysis of the results thereof will be described in detail. Thereafter, as an embodiment, the outline of an uncomfortableness threshold value estimation system, as well as its construction and operation, will be described.

(Explanation of Experimental Conditions)

2. UCL Subjective Report Experiment and Electroencephalogram Measurement Experiment 2-1. UCL Subjective Report Experiment The experimental participants were 12 adults, who were no longer in school, having normal hearing (28 to 49 years old).

The subjective report experiment was conducted before and after the electroencephalogram measurement experiment. Similarly to Non-Patent Document 1, continuous sounds were presented by ascending method using an audiometer, and an uncomfortably loud sound pressure was reported, this sound pressure being defined as the UCL. For each of three frequencies (1000, 2000, 4000 Hz) to be presented in the electroencephalogram measurement experiment, measurement was taken for both ears, one ear at a time. In order to prevent anticipation of the sound pressure, the sound pressure at the start of the experiment was randomly selected from among 60, 65, and 70 dB. The sound pressure of the continuous sound ascended by every 5 dB. An uncomfortably loud sound pressure was reported by raising a hand. Immediately after the participant raised a hand, the sound presentation was stopped, and the sound pressure was recorded.

Hereinafter, results of the subjective report experiment will be described.

The results of the subjective report experiment greatly differed from individual to individual, although all participants were people with normal hearing, with the largest difference of 40 dB at the same frequency. This indicates that the definition of "uncomfortably loud" may greatly from individual to individual.

FIG. 1 shows UCL evaluation results measured through subjective reporting. The subjective report experiment conducted before the electroencephalogram experiment for all test subjects showed a mean uncomfortableness threshold value of 91.2 dB. On the other hand, the subjective report experiment conducted after the electroencephalogram experiment showed a mean value of 94.0 dB. An overall mean value of the results from before and after the electroencephalogram experiment was 92.6 dB. It is also a characteristic of any UCL evaluation made through subjective reporting that there the mean value will vary and that the report value will fluctuate even when the same assessment is repeated over again. As shown in FIG. 1, the amount of fluctuation occurring before and after the experiment is 3.75±3.89 dB; thus, it can be seen that there is some fluctuation in the UCL evaluation through subjective reporting.

2-2. Electroencephalogram Measurement Experiment

In the electroencephalogram measurement experiment, paired stimulations were presented at a plurality of sound pressure levels, which were expected to include sound pressure levels, including UCL, and changes in characteristic features of the event-related potential in response to the first sound and the second sound were examined. Hereinafter, with reference to FIG. 2 to FIG. 6, experimental setting and experimental results of the electroencephalogram measurement experiment will be described.

FIG. 2 outlines the protocol of the electroencephalogram measurement experiment. The horizontal axis in FIG. 2 represents points in time. The sound stimulations were toneburst sounds with a duration of 50 ms. Each sound had a rise and fall of 3 ms. In order to examine event-related potentials for different frequencies and different sound pressure levels, sound stimulations of five sound pressure levels (80, 85, 90, 95, 100 dB) were prepared for each of three frequencies (1000, 2000, 4000 Hz). Headphones were used for presenting the sound stimulations. Although the headphones had two loudspeakers to be placed on the respective ears, each sound stimulation was presented to one ear at a time, rather than both ears. As paired stimulations, i.e., a first sound and a second sound, the same sound stimulation was successively presented twice to the same ear, with a predetermined interval therebetween. Then, a first sound and a second sound, which were identical sound stimulations, were presented to the same ear of each experimental participants, at a predetermined interval.

The participants were instructed that there was no need to pay attention to the sound stimulations. The interval between the first and second sounds in one pair of stimulations (intra-pair interval) was fixed at 300 ms. On the other hand, the interval between the first sound of one pair of stimulations and the first sound of a next pair of stimulations (interval between pairs of stimulations) was randomly determined within a range of 1000±200 ms. Two blocks of experiments were conducted, where 750 pairs of stimulations constituted one block.

The sound stimulations to be presented as paired stimulations were determined under the following constraints.

(i) No sound stimulations of the same frequency as that of immediately previous paired stimulations are selected.

(ii) The ear to which the paired stimulations are presented is randomly chosen between the right or left ear. However, not more than four pairs of stimulations are presented successively to either the right or left ear.

It was believed that these constraints alleviate the influence of taming (habituation) of auditory evoked potentials that is associated with successive presentation of the same paired stimulations.

Figure 3A:
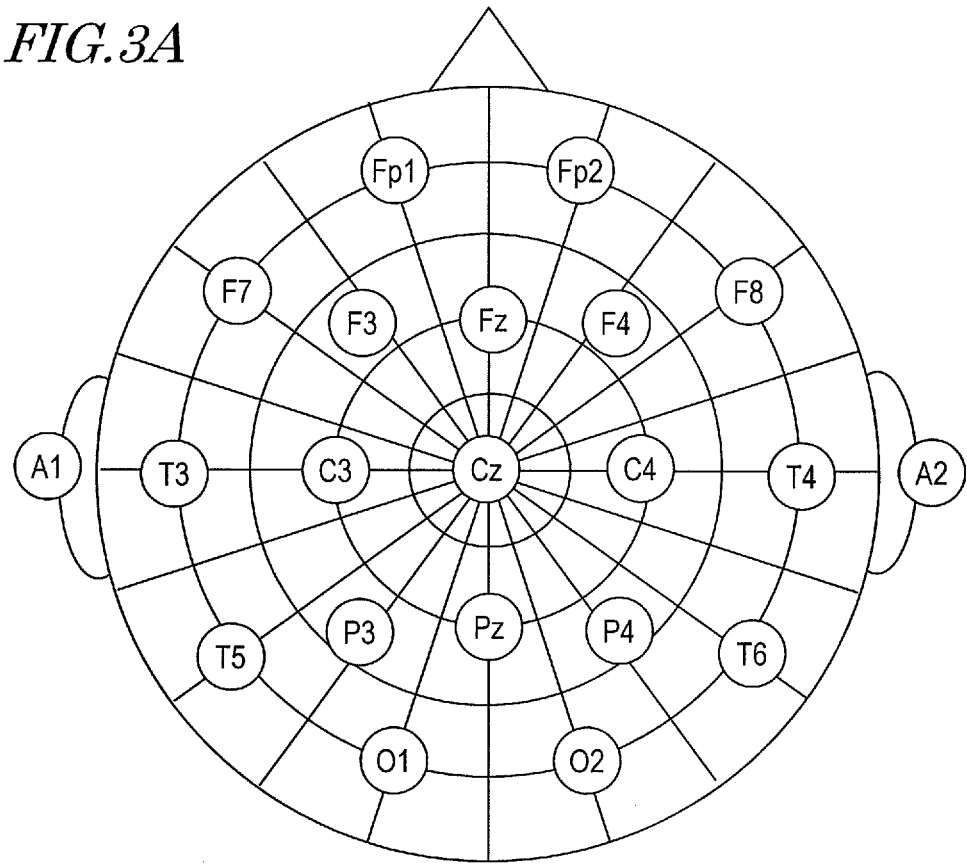
FIG. 3A is a diagram showing electrode positions according to the International 10-20 system (10-20 System).
Figure 3B:
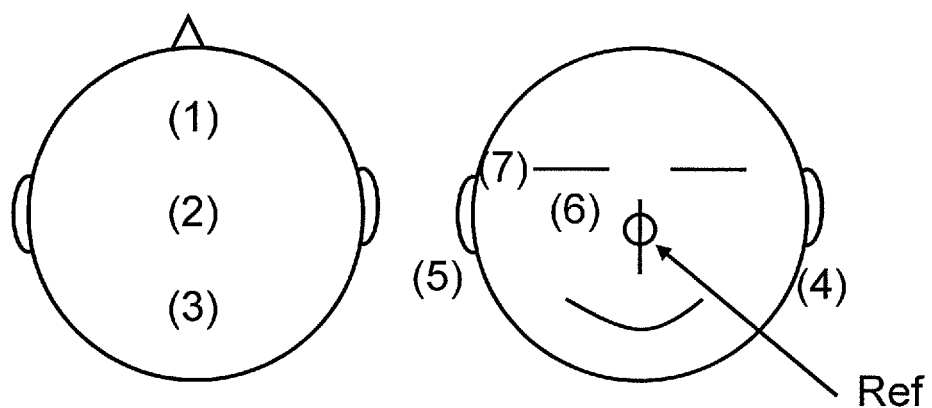
FIG. 3B is a diagram showing electrode positioning in the present experiment.

The electroencephalogram was recorded based on the nose, from Fz, Cz, Pz on the scalp (according to the International 10-20 system), the right side of the right eye, under the right eye, or the right or left mastoid. A "mastoid" is a protrusion of the cranium below the hind root of an ear. FIG. 3A is a diagram showing the electrode positions according to the International 10-20 system (10-20 System). FIG. 3B shows electrode positioning in the present experiment, where the following positions are shown: (1) Fz; (2) Cz; (3) Pz; (4) the left mastoid; (5) the right mastoid; (6) under the right eye; and (7) the right side of the right eye.

The sampling frequency was 1000 Hz; the time constant was 1 second; and an analog low-pass filter was applied at 30 Hz. It was subjected to a 5 to 20 Hz digital band-pass filter off-line, and re-referenced on the basis of linked mastoids. As an event-related potential in response to each sound stimulation, a waveform from −100 ms to 400 ms was cut out based on the point in time of presenting the first sound or second sound as a starting point. As used herein, "−100 ms" means a point in time which is 100 milliseconds before the point in time at which a sound stimulation was presented.

In order to examine the tendency of the overall electroencephalographic traits for different sound pressures, an arithmetic mean of event-related potentials of each individual person, in response to the first and second sounds, was taken with respect to each of the right and left ears, each frequency, and each sound pressure level. Those trials which exhibited an amplitude with an absolute value or 50 µV or more at any electrode were excluded from the total arithmetic mean or arithmetic mean, because noises such as electrooculographic potential might be mixed therein.

FIG. 4A(a) shows three kinds of total arithmetic mean waveforms obtained based on an event-related potential after presenting a first sound. A broken line, a thin solid line, and a bold solid line show examples of resultant electroencephalogram waveforms, i.e., total arithmetic mean waveforms of event-related potential obtained by presenting sound stimulations at 90, 95, and 100 dB, respectively. On the other hand, FIG. 4A(b) shows three kinds of total arithmetic mean waveforms obtained based on an event-related potential after presenting a second sound. Although an N1 component (negative peak) is indeed induced at about 100 ms after the sound stimulation presentation for the sound stimulations at all sound pressures, it can be seen that there are waveform differences between the first sound and the second sound.

Each event-related potential has been subjected to baseline correction so that an average potential in a zone from −100 ms to 0 ms since the timing of presentation equals 0 µV, thereby facilitating comparison between the event-related potentials in terms of change from the stimulation presentation. Since the second sound is presented 300 ms after the first sound begins to be presented, naturally there is some overlap between the event-related potential in response to the first sound and the event-related potential in response to the second sound acquired. Yet, the reason for the apparent lack of perfect coincidence between their waveforms around 300 ms in (a) and 0 ms in (b) in FIG. 4A is that, when obtaining an event-related potential in response to the second sound, a baseline correction is made based on the timing of presenting the second sound as a starting point. Hence, it may be assumed that the respective event-related potentials contain different information.

Hereinafter, results of the electroencephalogram measurement experiment will be described.

The inventors have decided that a characteristic feature for use in the estimation of an uncomfortableness threshold value be extracted in the form of a characteristic amount of event-related potential. More specifically, this characteristic amount is extracted as a characteristic amount concerning temporal changes in the frequency of event-related potential. Wavelet analysis was employed as a means of extraction because, presumably, wavelet analysis would make available not only time information but also specific frequency information within the time zone for analysis. The target of analysis was: (in terms of time) the event-related potential of a 10 ms zone before and after a time slot in which an N1 component peak was observed; and (in terms of frequency band) an average of output values from 5 Hz to 15 Hz, which is expected to contain response to sounds.

In FIG. 4B, (a) and (b) show results 21 and 22 of plotting characteristic amount changes in response to different sound pressures at presentation. The analysis was made by ascertaining wavelet coefficients for responses to the first sound and responses to the second sound. FIG. 4B(a) is a graph (indicated in wavelet coefficient values) showing changes in event-related potential waveform after presentation of the first sound, with respect to different sound pressures. FIG. 4B(b) is a graph (indicated in wavelet coefficient values) showing changes in event-related potential waveform after presentation of the second sound, with respect to different sound pressures. In each graph, the horizontal axis represents sound pressure of presentation, the louder sounds being registered more toward the right, and the vertical axis represents each characteristic amount (wavelet coefficient value).

Each graph shows three lines. These respectively represent three groups of test subjects, the grouping made based on the relative size of the UCL value through subjective reporting, where the characteristic amounts within each group are averaged. The respective lines show plotting of a test subject group with UCL of 100 dB or above, a test subject group with UCL on the order of 90 dB, and a test subject group with UCL 90 dB or below, all in average.

The inventors have arrived at the following concept from the data of FIG. 4B.

Firstly, the response to the first sound has its characteristic amount increasing as the presentation sound pressure increases. Graph 21 indicates an ascending trend toward the right for every test subject group, showing that the response to the first sound profusely contains response related to sound loudness.

By using N1P2 amplitude, the inventors have examined whether there exists a similar tendency to that of the wavelet coefficient mentioned above. An N1P2 amplitude refers to the absolute value of a difference between the peak potential of an N1 component and the peak potential of a P2 component (unit: µV). Specifically, N1P2 amplitude can be derived as a sum of the absolute value of an N1 peak potential (minus), and a P2 peak potential (plus). Based on the derived N1P2 amplitude, the inventors have confirmed a similar tendency concerning N1P2 amplitude also.

On the other hand, the response to the second sound does not exhibit a clear relationship between presentation sound pressure and size of the characteristic amount. In graph 22, changes in the characteristic amount with respect to changes in sound pressure are not very clear. However, the relationship between the sizes of characteristic amounts of one test subject group and another is rather clear. For example, in the test subject group associated with the largest UCL values in subjective reporting (100 dB or above), the characteristic amount appears to be the greatest. In the test subject group associated with the smallest UCL values in subjective reporting, the characteristic amount appears the smallest. In the test subject group associated with intermediate UCL values in subjective reporting (on the order of 90 dB), the characteristic amount appears intermediate.

From these analytical results, the inventors have made the following findings. The stimulation of the second sound is provided at 300 ms after the presentation of the first sound, which implies that the brain response to the stimulation of the first sound is not sufficiently completed by the time when the stimulation of the second sound is presented. Thus, it is considered that the response to the stimulation of the second sound is different from the response to the stimulation of the first sound.

The response to the stimulation of the first sound may well be regarded as a response to the sound loudness because, according to FIG. 4B(a), the waveform is on an increase in proportion to the sound loudness (see the blank arrow in FIG. 4B(a)) as a general tendency. On the other hand, the response to the stimulation of the second sound does not reflect sound loudness because, according to FIG. 4B(b), the waveform is not on any increase in proportion to the sound loudness (see the blank arrow in FIG. 4B(b)) as a general tendency. As described earlier, it can be said that the waveform of FIG. 4B(b) indicates the presence of a signal that is correlated with UCL even while the sound is not loud. Thus, it can be considered that the response to the second sound is one that is not directly related to sound loudness itself, but is related to the readiness of response with respect to sound loudness. Thus, it can be concluded that correlation exists between a UCL value from subjective reporting and the value of an event-related potential corresponding to the response to the second sound.

Based on this concept, correlation with the UCL value can be observed even when a loud sound is not being presented, e.g., near 85 dB in FIG. 4B(b). This means that a UCL value is estimatable without presenting overbearing sounds.

In related studies, it is known that the latency and N1-P2 amplitude of an N1 component in response to a pure-tone auditory stimulation (tone pip, toneburst) change in accordance with the intensity and rise time of the sound stimulation (see Suzuki et al., 1985, CHOSEI NOKANHANNO—SONOKISOTO RINSHO—, or "Auditory Brain Stem Response—Its Basics And Clinical Applications—, MEDICAL VIEW CO., LTD., pp. 384-385). Specifically, within the range of sound pressure levels that are smaller than a predetermined sound pressure level, the latency of the N1 component decreases and the N1-P2 amplitude increase as the intensity of the stimulation sound increases. Moreover, at or above the predetermined sound pressure level, the decrease in the N1 component latency and the increase in the N1-P2 amplitude become saturated. This tendency can also be observed in FIG. 4B(a). However, it can be seen that the characteristic amount associated with the second sound is different in behavior from the first sound.

2-3. UCL Estimation Experiment Based on Data from Both Experiments

Based on this concept, an experiment was conducted to estimate UCL by analyzing the characteristic amount of event-related potential in response to a presented sound stimulation, and confirm how well the estimated UCL matched the UCL value from subjective reporting.

Figure 5:
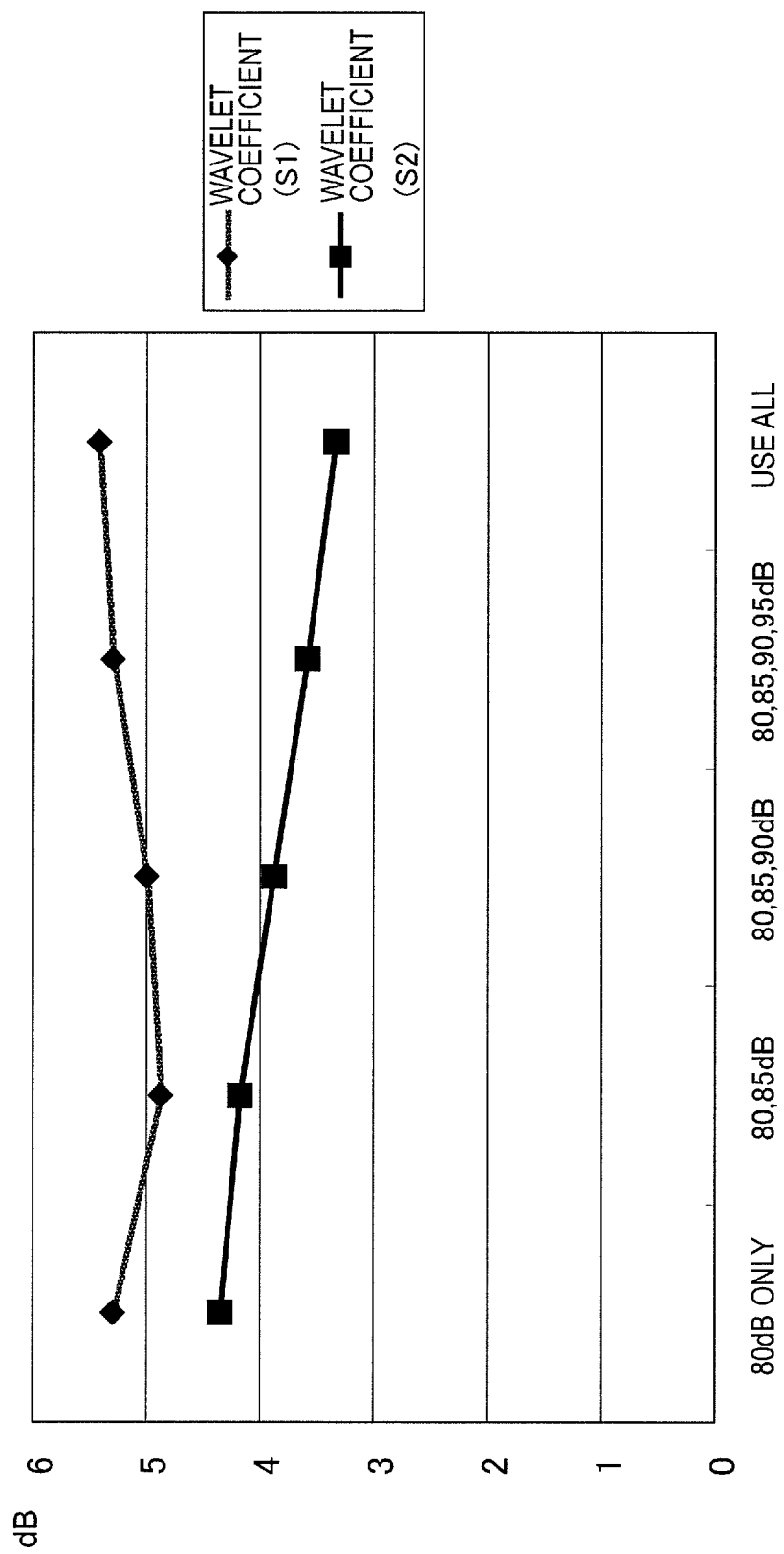
FIG. 5 is a graph of UCL estimation results.

FIG. 5 is a graph of UCL estimation results. The horizontal axis represents the sound pressure range of a presented sound stimulation(s) which produced an event-related potential(s) used in determining the wavelet coefficient. At the leftmost, only an event-related potential at 80 dB is used; next to it, event-related potentials at 80 dB and 85 dB are used; and increasingly more information is used toward the right, until at the right most is indicated a result of determining a wavelet coefficient by using event-related potentials in response to sound pressures of all of 80 to 100 dB (in 5 dB increments). The vertical axis represents how well the analytical UCL estimation results matched the subjective report values (average of errors). For example, if the subjectively-reported value was 90 dB and the estimated value was 85 dB or 95 dB, the error was calculated to be 5 dB. FIG. 5 shows plotting of an average of estimation errors of the respective test subjects at each frequency, calculated based on this notion.

FIG. 5 shows two lines: an upper line (S1) obtained by using the wavelet coefficients of event-related potentials in response to the first sound; and a lower line (S2) obtained by using the wavelet coefficients of event-related potentials in response to the second sound.

Since the vertical axis of FIG. 5 indicates an error between a UCL value from subjective reporting and an estimated UCL value, a smaller value thereof means a higher accuracy of estimation. This makes it preferable to use the event-related potential to the second sound (lower line), which is prone to smaller estimation errors. For example, regarding the rightmost instance on the horizontal axis in FIG. 5 (where event-related potentials to all sound pressures are used), the difference between when the event-related potential in response to the first sound is used and when the event-related potential in response to the second sound is used is about 2 dB; this means the estimation error being smaller by 2 dB, indicative of a more precise estimation closer to the subjective reporting.

The UCL was estimated by using discriminant analysis technique. In this assessment, a distinguisher was constructed, which used pairs of event-related potentials and subjectively-reported UCL values of test subjects other than the target of assessment as learning data. The distinguisher thus constructed was used to make a UCL estimation for the target of assessment.

As a result, as FIG. 5 indicates, there were smaller errors when the wavelet coefficient from the second sound was used. Also, FIG. 1 indicates a 3.75±3.89 dB fluctuation existing between the subjectively-reported UCL values before and after the experiment. Some of the UCLs estimated by using the wavelet coefficient from the second sound had smaller fluctuations than did the subjectively-reported UCL values, namely, at the presentation sound pressures of 80 dB, 85 dB, 90 dB, or when any more data amount was used.

Figure 6:
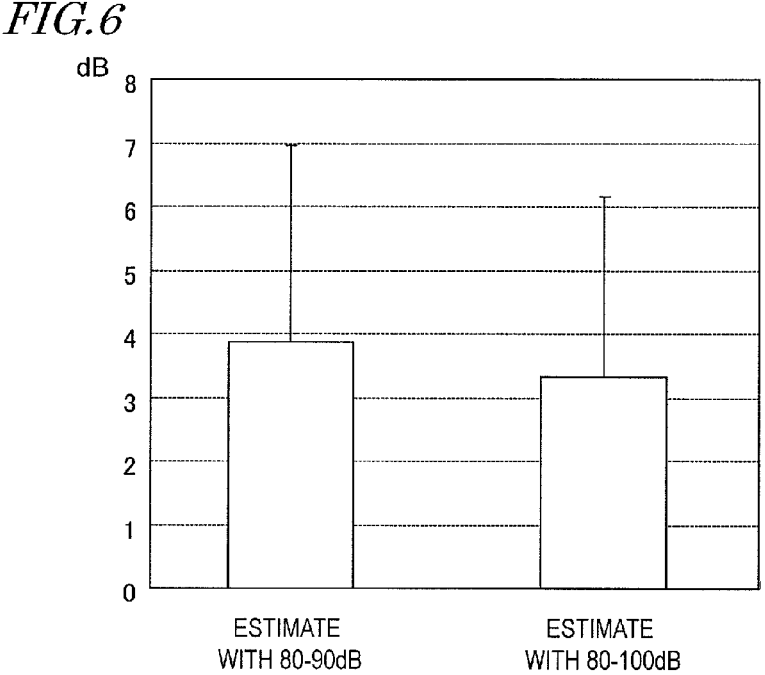
FIG. 6 is a graph showing results of an estimation error comparison.

FIG. 6 shows results of an estimation error comparison. The horizontal axis indicates data used for the estimation. The vertical axis indicates estimation errors from the subjective UCLs in dB. Thus, even when estimation was made from the event-related potentials to the sound pressures of 80, 85, and 90 dB alone, a similar level of estimation was attained to making estimation by using the event-related potentials to all sound pressures, with an error size being about the same as the fluctuations in subjective reporting (FIG. 1).

From the above experiment, the inventors have made the finding that a UCL value can be estimated based on induced responses when two sounds of the same frequency and the same sound pressure (the first and second sounds) are presented. Specifically, an electroencephalogram in response to the first sound mainly contains a component corresponding to sound loudness, whereas an electroencephalogram in response to the second sound contains a component corresponding to UCL. Thus, the inventors' finding is that, by analyzing an electroencephalogram (event-related potential) in response to the second sound, a UCL value can be estimated with a sufficient precision.

Hereinafter, an embodiment of an uncomfortableness threshold value estimation system constructed based on these characteristics found by the inventors will be described in detail, with reference to the figures.

3. Description of an Illustrative Embodiment of the Present Disclosure

Figure 7:
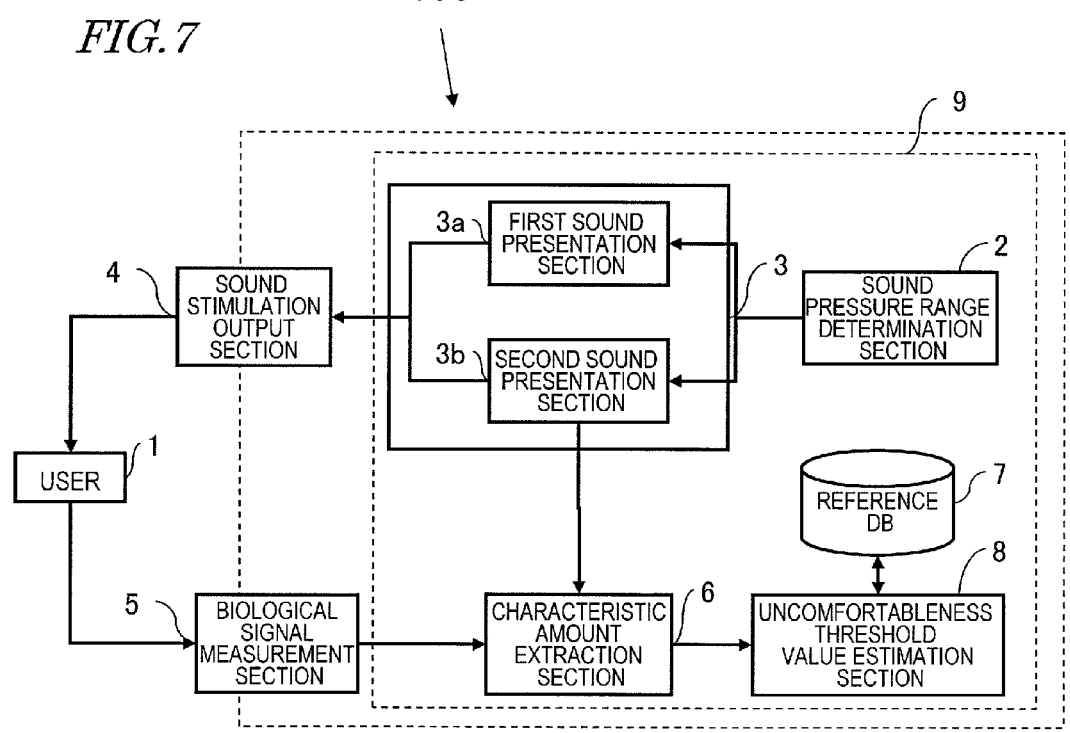
FIG. 7 is a block diagram showing the construction of an uncomfortableness threshold value estimation system 100 according to an illustrative embodiment.

FIG. 7 shows the construction of an uncomfortableness threshold value estimation system 100. The uncomfortableness threshold value estimation system 100 includes a sound pressure range determination section 2, a presentation sound control section 3, a sound stimulation output section 4, a biological signal measurement section 5, a characteristic amount extraction section 6, a reference database (DB) 7, and an uncomfortableness threshold value estimation section 8. Note that a user 1 is illustrated for reference sake.

The sound pressure range determination section 2 determines a sound pressure range for sound stimulations to be presented to the user 1.

In the presentation sound control section 3, the presentation sound is controlled in accordance with the sound pressure range determined by the sound pressure range determination section 2. The presentation sound control section 3 includes a first sound presentation section 3a and a second sound presentation section 3b. Through control of the first sound presentation section 3a and the second sound presentation section 3b, the presentation sound control section 3 controls presentation of the first and second sounds, in accordance with the sound pressure range determined by the sound pressure range determination section 2. Note that this sound pressure range is determined mainly in order to define an upper limit of the sound pressure of the presentation sound.

The sound stimulation output section 4 receives an audio signal as controlled by the presentation sound control section 3, and presents sound stimulations to the user with a frequency and sound pressure based on that audio signal. The sound stimulation output section 4 is a device which presents sound stimulations, e.g., headphones or a loudspeaker(s).

The biological signal measurement section 5 measures an electroencephalogram of the user 1. The biological signal measurement section 5 is composed of an electroencephalograph or the like which includes electrodes that are worn by the user 1. From the second sound presentation section 3b in the presentation sound control section 3, the characteristic amount extraction section 6 receives information of the timing with which the second sound was presented, acquires an event-related potential from the electroencephalogram which is acquired from the biological signal measurement section 5, and accumulates it. An event-related potential is a potential fluctuation of an electroencephalogram which occurs in response to a stimulation. An event-related potential may be of different types as to: (1) polarity of potential (plus or minus), (2) latency (the amount of time after a stimulation is generated until a potential fluctuation occurs); (3) amplitude level of potential; and so on. Each different type of signal contains different information concerning the user 5. By referring to a criterion for making an uncomfortableness threshold value estimation that is retained in a reference DB 7, the uncomfortableness threshold value estimation section 8 estimates an uncomfortableness threshold value, by using data which is accumulated in the characteristic amount extraction section 6.

Note that the construction including the sound pressure range determination section 2, the presentation sound control section 3, the characteristic amount extraction section 6, the reference DB 7, and the uncomfortableness threshold value estimation section 8 may be implemented as a single signal processing circuit (electronic circuit). In the present embodiment, such a signal processing circuit will be referred to as an uncomfortableness threshold value processing circuit 9.

Figure 8:
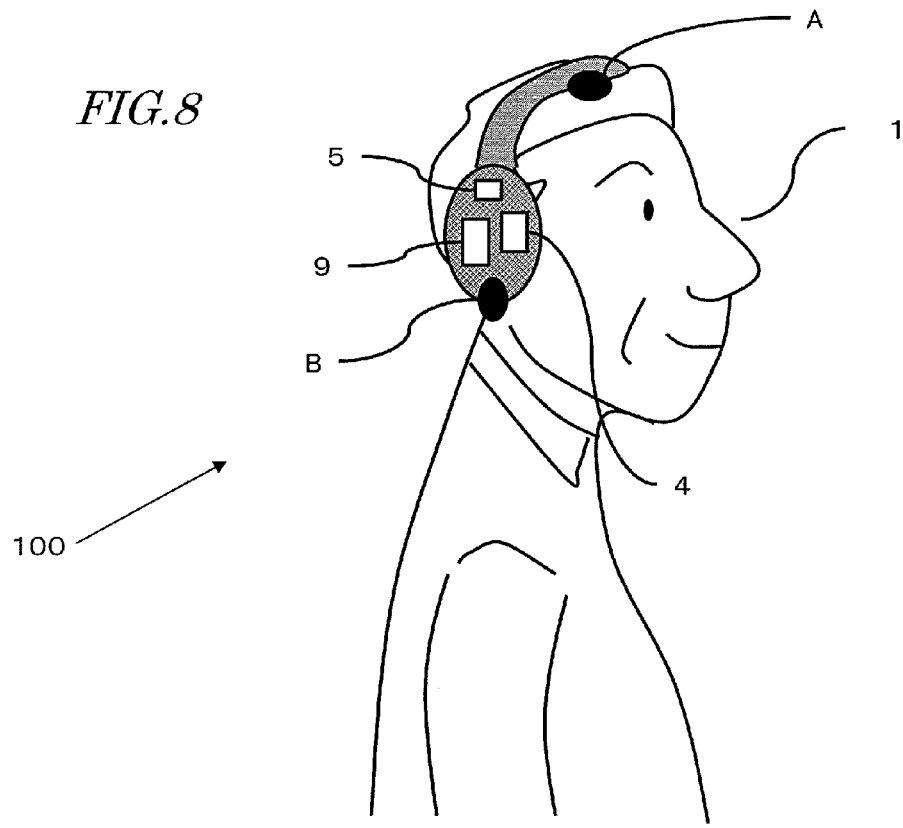
FIG. 8 is a diagram showing an exemplary specific implementation of the uncomfortableness threshold value estimation system 100.

FIG. 8 shows an exemplary specific implementation of the uncomfortableness threshold value estimation system 100. In this example, the entire uncomfortableness threshold value estimation system 100 is incorporated in a headphone-type housing. Such an uncomfortableness threshold value estimation system 100 may be used, before the user 1 purchases a hearing aid, for assessing his or her hearing, including the uncomfortableness threshold value, for example. The user 1 wears the uncomfortableness threshold value estimation system 100 on his or her head.

The uncomfortableness threshold value estimation system 100 shown in FIG. 8 includes the sound stimulation output section 4, the biological signal measurement section 5, and the uncomfortableness threshold value processing circuit 9.

The biological signal measurement section 5 is connected in a wired or wireless manner to at least two electrodes A and B for electroencephalogram measurement. An electroencephalogram is a potential change on the head. Therefore, in order to measure an electroencephalogram, electrode A and electrode B need to be in contact with the head at predetermined positions. It is desirable that electrode A and electrode B are shaped so as to facilitate contact with the predetermined positions on the head. In the present specification, predetermined positions on the head are meant to be positions that are suitable for hearing assessment. According to designations under the International 10-20 electrode system (FIG. 3A), these positions are Cz, C3, C4, etc., on the parietal, for example. By allowing a leading electrode (e.g., electrode A for electroencephalogram measurement) to be in contact with any of these positions, it is believed that induced responses to sounds can be easily recorded. Note that the electrode positions may vary depending on the electroencephalogram to be acquired. The other electrode (electrode B for electroencephalogram measurement) may be placed as a ground electrode or a reference electrode at A2 or A1 position in the International 10-20 electrode system, for example. Thus, an electroencephalogram can be derived.

To the right or left ear of the user 1, the uncomfortableness threshold value estimation system 100 sequentially presents paired stimulations of the same frequency and the same sound pressure, and by looking at the electroencephalogram (event-related potential) response of the user 1 which is measured based on the point of presenting the second sound as a starting point, applies the criterion in the reference DB 7 (in which a criterion for UCL estimation is stored) to estimate an uncomfortableness threshold value of the user 1.

The biological signal measurement section 5 measures the electroencephalogram of the user 1 that corresponds to a potential difference between electrode A and electrode B. The biological signal measurement section 5 sends information (electroencephalogram signal) corresponding to the potential difference to the uncomfortableness threshold value processing circuit 9. Although the uncomfortableness threshold value processing circuit 9 is shown in FIG. 8 to be in the same housing as the sound stimulation output section 4 and the biological signal measurement section 5, the uncomfortableness threshold value processing circuit 9 may be provided in a separate housing. In that case, the electroencephalogram signal which is measured by the biological signal measurement section 5 may be sent in a wireless or wired manner to the uncomfortableness threshold value processing circuit 9.

Figure 9:
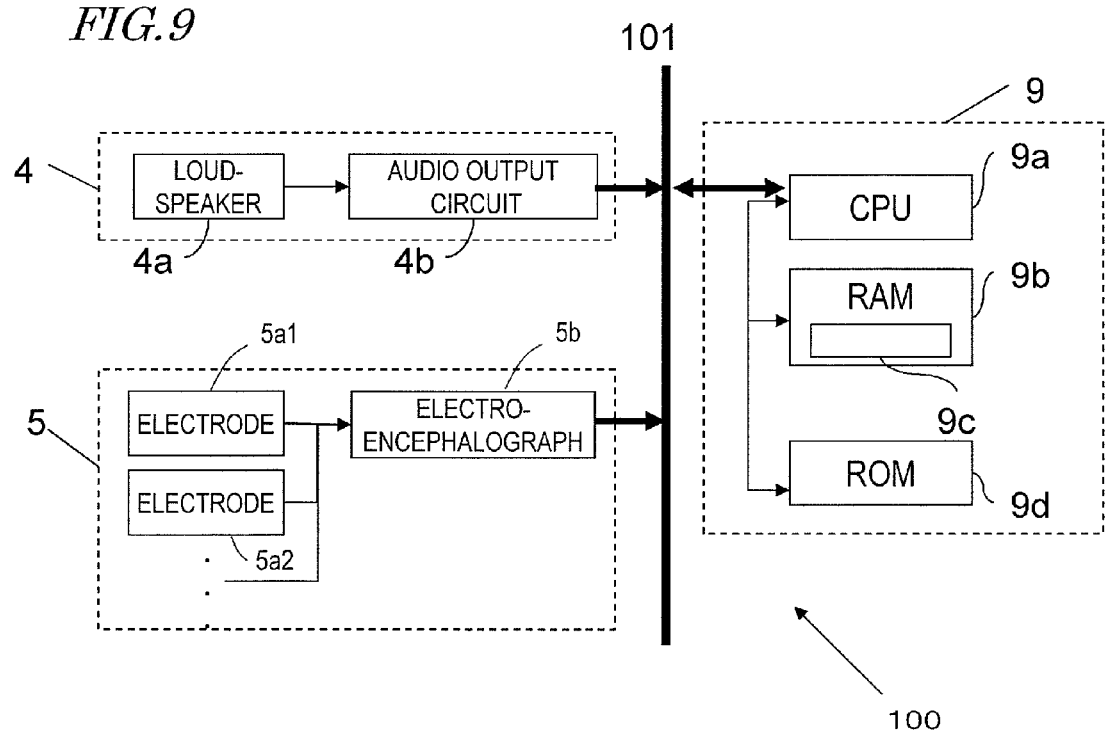
FIG. 9 is a diagram showing the hardware construction of the uncomfortableness threshold value estimation system 100 according to an illustrative embodiment.

FIG. 9 shows the hardware construction of the uncomfortableness threshold value estimation system 100 according to the present embodiment. The sound stimulation output section 4, the biological signal measurement section 5, and the uncomfortableness threshold value processing circuit 9 are connected to one another via a bus 101, so as to be capable of data exchange therebetween.

The uncomfortableness threshold value processing circuit 9 is realized as a processing circuit which has a CPU 9a, a RAM 9b, a program 9c, and a ROM 9d. For example, the CPU 9a reads from the ROM 9d the program 9c stored therein, and unfolds it on the RAM 9b. The CPU 9a executes the computer program 9c stored in the RAM 9b. The computer program 9c states instruction code for causing the CPU 9a to execute a process which is in accordance with the procedure shown in a flowchart described later. As a result of this, the CPU 9a functions as the uncomfortableness threshold value processing circuit 9. As will be described later, the uncomfortableness threshold value processing circuits 9 performs an uncomfortableness threshold value estimation and more by utilizing the reference DB 7, which is stored in the same RAM 9b or in a separate storage medium (not shown). This process will be described later.

The sound stimulation output section 4 includes a loudspeaker 4a and an audio output circuit 4b. In accordance with an instruction from the CPU 9a, the audio output circuit 4b outputs each sound stimulation to be presented at a designate sound pressure, via the loudspeaker 4a.

The biological signal measurement section 5 includes an electrode 5a1, an electrode 5a2, and an electroencephalograph 5b. The electrodes 5a1 and 5a2, which are connected to the electroencephalograph 5a, are worn on the head of the user 1. The measured electroencephalogram data is sent to the CPU 9a via the bus 101, so as to be accumulated in the RAM9c in the form of event-related potentials.

Note that the uncomfortableness threshold value processing circuit 9 may be realized as a piece of hardware composed of a single semiconductor circuit having a computer program therein, e.g., a DSP. Moreover, the audio output circuit 4b and the electroencephalograph 5b can also be together implemented on a single integrated circuit.

The aforementioned computer program 9c may be distributed on the market in the form of a product recorded on a storage medium such as a CD-ROM, or transmitted through telecommunication lines such as the Internet. Upon reading the computer program 9c, a device having the hardware shown in FIG. 9 (e.g., a PC) is able to function as the uncomfortableness threshold value estimation system 100 according to the present embodiment.

Next, the processing by this uncomfortableness threshold value estimation system will be described in detail with reference to FIGS. 10 to 21.

(Outline of Overall Process)

Figure 10:
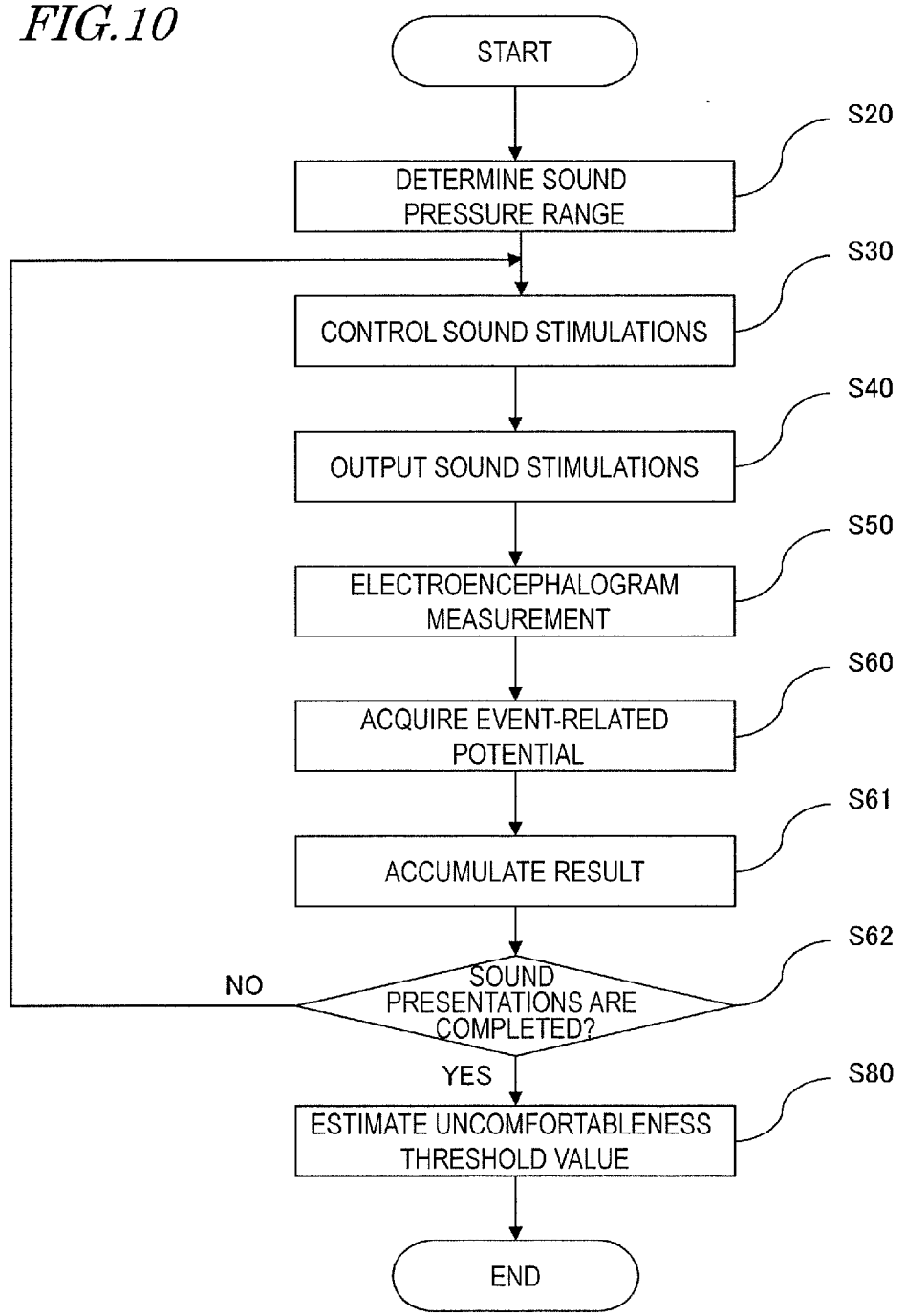
FIG. 10 is a flowchart outlining a processing procedure by the uncomfortableness threshold value estimation system 100 according to an illustrative embodiment.

FIG. 10 outlines a processing procedure by the uncomfortableness threshold value estimation system 100 of the present embodiment. Those steps which require more than outline description will be described with reference to a more detailed flowchart later.

At step S20, the sound pressure range determination section 2 determines a sound pressure range in which to make presentations to the user 1. In order to realize an uncomfortableness threshold value estimation with little burden on the user 1, a range of presentation sound pressure which will not distress the user 1 is to be chosen. The method of determining a maximum value of presentation sound pressure (i.e., a maximum value of the sound pressure range) may be as follows, for example. In the case where any sound louder than 80 dB is defined by law as noise, the maximum value may be set to 80 dB or less, thus citing the commonly-used noise limit value. Alternatively, from the hearing threshold value (HTL) of the user 1 who is the target of uncomfortableness threshold value estimation, a range which is presumed to be safe (a threshold value defining the upper limit) may be determined. Conventional techniques for estimating a UCL from an HTL include the NAL-R method, the MCL mirror method, and the like; a value which is 10 dB or 20 dB lower than a UCL value that is expected from such techniques may be set as the maximum value of presentation sound pressure. On the other hand, a minimum value of presentation sound pressure may be chosen to be 10 dB smaller than the earlier-determined maximum value of presentation sound pressure, for example. Based on this principle, in the earlier example, the maximum value of presentation sound pressure will be determined as 80 dB, and the minimum value as 70 dB. In this case, the presentation sound pressures can be chosen to the following three: 70 dB, 75 dB, and 80 dB.

At step S30, within the sound pressure range determined by the sound pressure range determination section 2, the presentation sound control section 3 controls sound stimulations to be presented to the user 1. The sound stimulations are provided in the form of two sounds which are successively presented at a predetermined interval. In the present specification, such two successively-presented sound stimulations will be referred to as paired stimulations. The presentation sound control section 3 at least controls the frequency and sound pressure of sounds. Note that the presentation sound control section 3 may control: which ear of the user 1 the sound stimulations are to be presented; the interval between the first and second sounds of a pair of stimulations; the interval between two pairs; and so on. In the present specification, even if the first and second sounds are of sound pressures with a difference that is not aurally distinguishable to humans, the first and second sounds are regarded as having the same sound pressure.

In the above description of the illustrative embodiment, the interval from after a first sound in the pair of stimulations is presented and before a second sound is presented is assumed to be 300 ms, for example. This is because the interval between the first and second sounds in the pair of stimulations must ensure that a response to the first sound and a response to the second sound will be clearly induced. However, it is presumable that this goal may be attained when it is 100 ms or more, for example, which means that it may be 200 ms, for another example. In view of the fact that an N1 component may appear in a range of 100±50 ms after the first sound is presented, the second sound may be presented at 150 ms or later following the presentation of the first sound. In order to allow for individual differences, an error of about 100 ms may be tolerated. Taking all of these into consideration, after the first sound of a pair of stimulations is presented, the second sound may be presented at an interval which is in the range from 100 ms to 400 ms, whereby the uncomfortableness threshold value estimation system 100, etc., of the above embodiment should be able to perform the aforementioned operation.

Moreover, the intra-pair interval may be set to any arbitrary value which is 1 second (1000 ms) or less, during which time the processing within the brain that was induced by the first sound is still presumed to be continuing. The earlier sound in a pair of stimulations, i.e., the first sound, is controlled by the first sound presentation section 3a, whereas the next sound, i.e., the second sound, is controlled by the second sound presentation section 3b. In accordance with the designated time of sound stimulation presentation, the second sound presentation section 3b outputs a trigger to the characteristic amount extraction section 6. Moreover, the information concerning the right or left ear, frequency, and sound pressure of the presented sound stimulations is also sent to the characteristic amount extraction section 6.

At step S40, the sound stimulation output section 4 presents the sound stimulations as determined by the presentation sound control section 3 to the user 1, with timing as determined by the presentation sound control section 3.

At step S50, the electroencephalogram measurement section 5 measures an electroencephalogram to acquire electroencephalogram data. The electroencephalogram measurement section 5 may measure an electroencephalogram of the user 1 only during a period in which electroencephalogram data is needed, or incessantly be measuring electroencephalograms.

At step S60, the characteristic amount extraction section 6 cuts out an event-related potential waveform from the electroencephalogram waveform, and accumulates the data. As a result, waveform data of an event-related potential(s) based on the timings of presenting sound stimulations which are sent from the presentation sound control section 3 as starting points is acquired.

The zone in which to acquire an event-related potential may be from −100 milliseconds to 400 milliseconds since the point of occurrence of an ambient sound, for example. The zone from −100 milliseconds to 0 milliseconds is used for baseline correction, whereas the zone from 0 milliseconds to 400 milliseconds is subject to assessment as representing a change in event-related potential. This zone of acquisition may fluctuate depending on the electroencephalogram component which is to be assessed. For example, in the case where an N1 component is mainly to be observed, which focuses on an electroencephalogram near 100 milliseconds, a zone from −100 milliseconds to 300 milliseconds may be acquired; or in the case where late components are also to be used, a zone from e.g. 100 milliseconds to 600 milliseconds may be acquired.

At step S61, the characteristic amount extraction section 6 accumulates the waveform data of the event-related potential(s) having been cut out at step S60 as an addition to the existing waveform data which is retained in the characteristic amount extraction section 6. As related attributes, the characteristic amount extraction section 6 also accumulates the information concerning the right or left ear, frequency, and sound pressure of sound stimulations, which is sent from the presentation sound control section 3. By allowing the sound attributes to be accumulated in association with the electroencephalogram data, it becomes possible to accumulate event-related potentials from plural instances corresponding to each attribute. Since an electroencephalogram signal is weak and is prone to noise mixing, it is necessary accumulate waveforms from plural instances under the same condition.

At step S62, the characteristic amount extraction section 6 determines whether sound stimulations have been presented a sufficient number of times, such that event-related potentials corresponding to each set of attributes have been sufficiently accumulated. If it is determined that such presentation of sound stimulations is complete, control proceeds to step S80; if not, control returns to step S30. As used herein, a "sufficient number of times" is a notion ensuring a precision which is necessary for uncomfortableness threshold value estimation. For example, in the present embodiment, twenty instances of accumulation of event-related potentials for each condition was stipulated as a condition of completion in the aforementioned experimentation. This number of times is chosen in accordance with the quality of the electroencephalogram signal and the estimation method; in the case of a high-quality electroencephalogram signal, a smaller number of summations, e.g., 5 or 10 instances, may suffice; an electroencephalogram signal in which a lot of noise is mixed, however, may presumably require summations over 30 times or more.

At step S80, the uncomfortableness threshold value estimation section 8 estimates an uncomfortableness threshold value of the user 1. As a specific method thereof, the uncomfortableness threshold value estimation section 8 may estimate an uncomfortableness threshold value of the user 1 from the event-related potential data accumulated in the characteristic amount extraction section 6, based on a criterion for uncomfortableness threshold value estimation that is retained in the reference DB 7. The uncomfortableness threshold value estimation is made with respect to each frequency of the presentation sounds and each of the right and left ears, for example, and the uncomfortableness threshold value is expressed as a sound pressure, e.g., 100 dB. When the uncomfortableness threshold value is 100 dB, it means that the user 1 hearing a sound of any sound pressure of 100 dB or above will feel uncomfortable. The details of the criterion that is retained in the reference DB 7 and the uncomfortableness threshold value estimation method will be described later.

Next, the processes by the presentation sound control section 3 (step S30), the characteristic amount extraction section 6 (steps S60, S61, S62), and the uncomfortableness threshold value estimation section 8 (step S80) in the aforementioned flow, which are of particular relevance to the description of the illustrative embodiment, will further be described in detail with reference to separate flowcharts and figures.

Figures 11, 12:
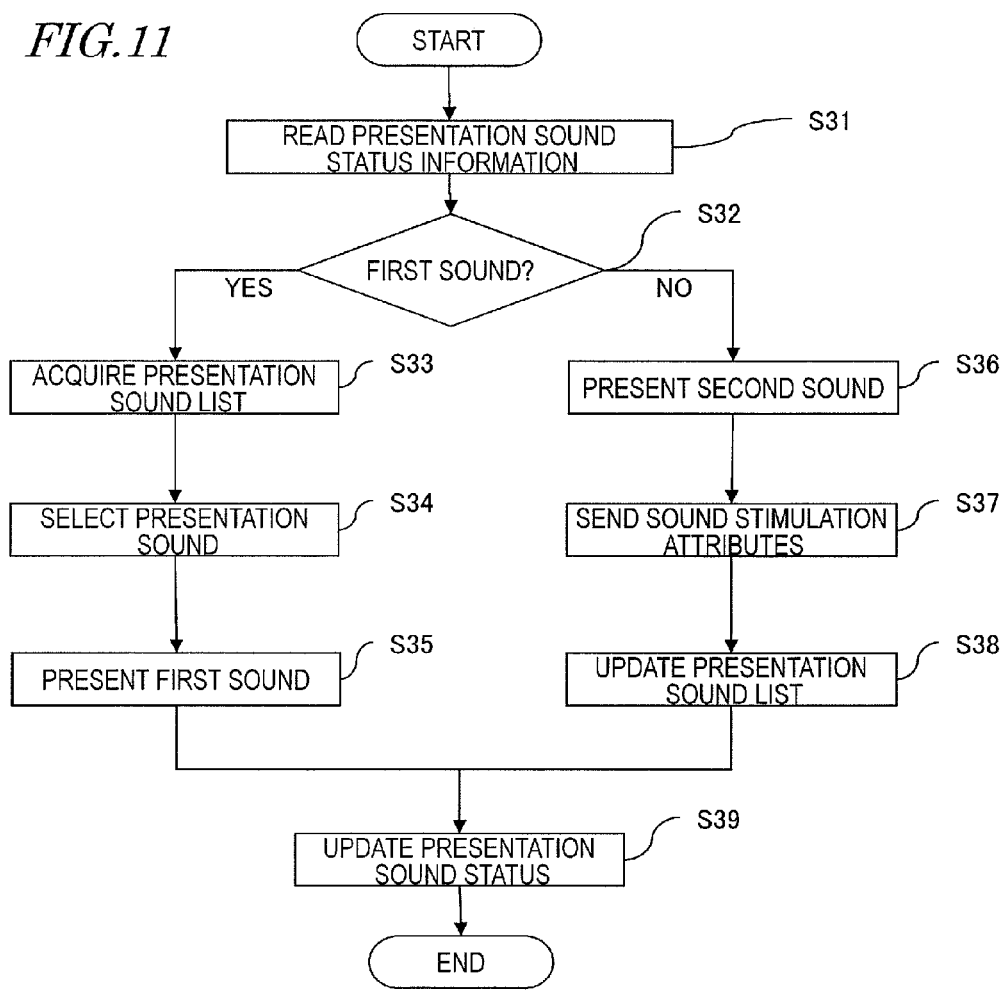
FIG. 11 is a flowchart showing details of processing by a presentation sound control section 3.
FIG. 12 is a diagram showing an exemplary data expression of a presentation sound list.

FIG. 11 shows details of the processing by the presentation sound control section 3. FIG. 12 shows an exemplary data expression of a presentation sound list. In accordance with the sound pressure range determined by the sound pressure range determination section 2, the presentation sound control section 3 sequentially presents a pair of stimulation sounds.

At step S31, the presentation sound control section 3 reads information representing a presentation sound status. As used herein, a "presentation sound status" refers to a state as to whether the first sound or the second sound is to be currently presented, and a value is retained in the presentation sound control section 3 as information representing this state. For example, a presentation sound status of 0 may indicate a state where the first sound is to be presented, and a presentation sound status of 1 may indicate a state where the first sound has already been presented and the second sound is now to be presented.

At step S32, based on the presentation sound status acquired at step S31, the presentation sound control section 3 determines whether the first sound is to be presented or not. If YES at step S32, control proceeds to step S33 to present the first sound; if NO, control proceeds to step S36 to present the second sound.

Steps S33 to S35 are process which are performed by the first sound presentation section 3a of the presentation sound control section 3.

At step S33, the first sound presentation section 3a acquires a presentation sound list. The presentation sound list is a recording of which sound stimulations have already been presented how many times, relative to an amount of sound stimulations that need to be presented for assessment. FIG. 12 shows an example of the presentation sound list.

The example of FIG. 12 illustrates exemplary data of the presentation sound list in the case where uncomfortableness threshold values are to be estimated for sounds at the frequencies of 1000 Hz, 2000 Hz, and 4000 Hz with respect to each ear. Given five sound stimulations of 70, 75, 80, 85, and 90 dB as decided through the sound pressure range determination, the number of sound presentations which have already been made is stated in each cell of the table. In an electroencephalogram-based uncomfortableness threshold value estimation process, an arithmetic mean is taken before making the estimation; therefore, in acquiring event-related potentials, it is necessary that sound stimulations be presented in plural instances under the same condition. The number of times of presenting sound stimulations may be 10, or 20, for example, which is subject to the content of assessment, the device used, the environment of measurement, and the like. FIG. 12 is an example of a presentation sound list which might be obtained after some time has passed since the beginning of assessment. It is illustrated that the first sound stimulation has already been presented (value "1") for some conditions, but that no sound stimulation has been presented (value "0") for other conditions. Every time a given sound stimulation completes presentation, the number in the presented cell increases by one, until the process is allowed to end when e.g. twenty is reached for every condition.

At step S34, the first sound presentation section 3a selects attributes for the sound stimulation to be presented. In the example of FIG. 12, the attributes of a sound stimulation indicate: the tested ear being right or left; the frequency being 1000 Hz, 2000 Hz, or 4000 Hz; and the presentation sound pressure being 70 dB, 75 dB, 80 dB, 85 dB, or 90 dB. The attribute selection is made so that, among the cells of the presentation sound list table, those having the smallest values are randomly selected, this being in order to ensure that sound stimulations of the same attributes will not be selected in succession.

At step S35, the first sound presentation section 3a sends sound stimulation data which is generated in accordance with the attributes selected at step S34 to the sound stimulation output section 4. In the case of simple stimulations such as pure tones, the sound stimulation data may be generated each time through calculation; or the sound stimulation data may be previously retained in memory, and data corresponding to given attributes may be acquired from the memory.

Steps S36 to S38 are executed by the second sound presentation section 3b.

At step S36, the second sound presentation section 3b sends sound stimulation data which is generated in accordance with the attributes selected at step S34 to the sound stimulation output section 4. The sound stimulation data may be generated each time through calculation; or the sound stimulation data may be previously retained in memory, and data corresponding to given attributes may be acquired from the memory.

At step S37, the second sound presentation section 3b sends the sound stimulation attributes to the characteristic amount extraction section 6. The "sound stimulation attributes" are information concerning the tested ear to which the sound stimulation is presented, the frequency of the sound stimulation, and concerning which sound pressure is presented at which timing. In the present embodiment, since an event-related potential in response to the second sound is to be used for uncomfortableness threshold value estimation, information that is needed for the acquisition and accumulation of this event-related potential is sent.

At step S38, the second sound presentation section 3b updates the presentation sound list. Upon completing presentation of the two sound stimulations, the number in the corresponding cell in the presentation sound list is increased by one.

At step S39, the presentation sound control section 3 updates the presentation sound status. After presentation of the first sound, the presentation sound status is updated from 0 to 1; after presentation of the second sound, the presentation sound status is updated from 1 to 0.

Thus, through such processes by the presentation sound control section 3, presentation of paired stimulations is realized. As the presentation timing, time intervals as illustrated in FIG. 2 may be adopted, for example.

Figure 13:
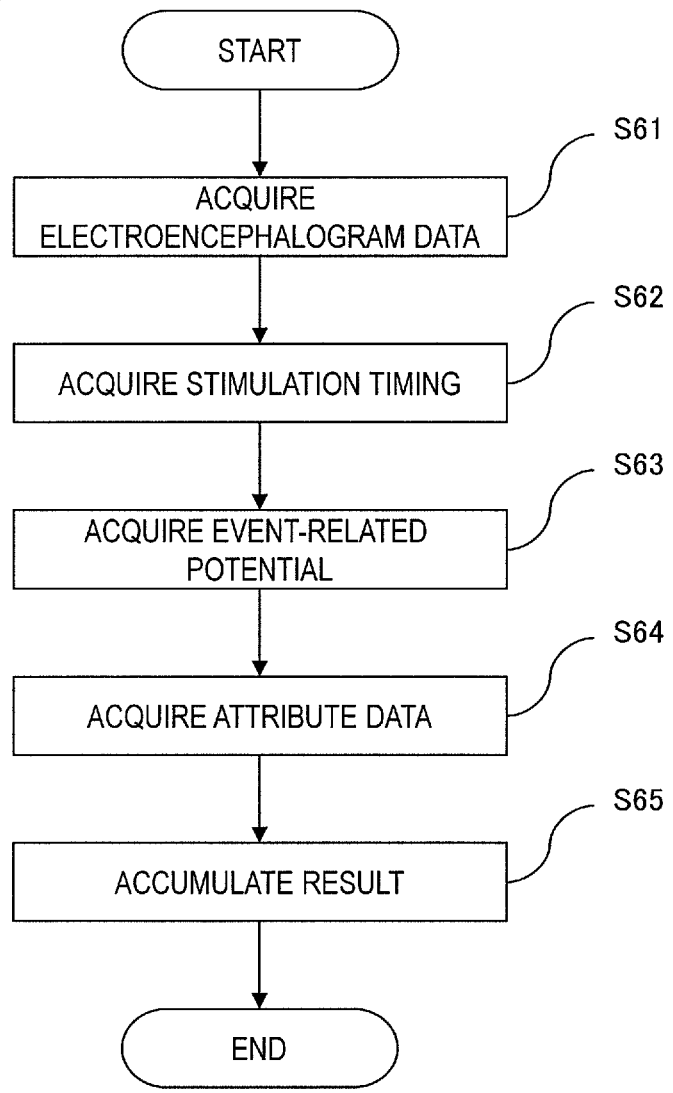
FIG. 13 is a flowchart showing processing by a characteristic amount extraction section 6.
Figure 14:
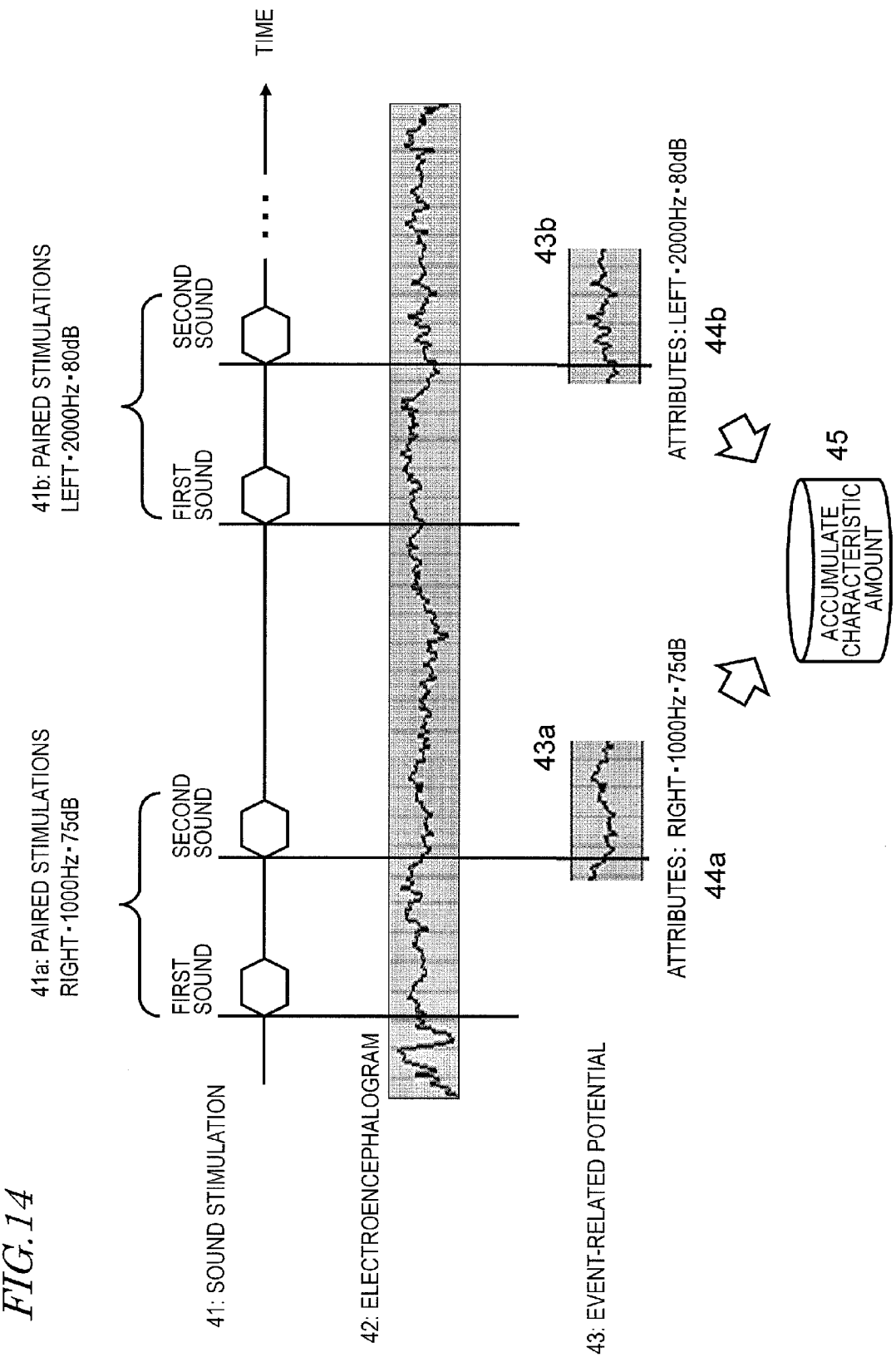
FIG. 14 is a schematic conceptional diagram showing an extraction process of characteristic amounts of event-related potentials.

Next, the processing by the characteristic amount extraction section 6 shown at steps S60 and S61 in FIG. 10 will be described in detail. This is where an induced electroencephalographic response of the user 1 to whom sound stimulations are presented is acquired and accumulated while being classified with respect to each condition of sound stimulations. FIG. 13 is a flowchart of processing by the characteristic amount extraction section 6. FIG. 14 is a schematic conceptional diagram showing an extraction process of characteristic amounts of event-related potentials.

At step S61, the characteristic amount extraction section 6 acquires electroencephalogram data which has been measured by the biological signal measurement section 5. The electroencephalogram data at this point is in the form of a data sequence that has been consecutively acquired based on the sampling frequency.

At step S62, from the second sound presentation section 3b, the characteristic amount extraction section 6 acquires information representing the timing with which to present the second sound. In the present embodiment, since an electroencephalogram response to the second sound is to be used for UCL estimation, information of this presentation timing is needed.

At step S63, the characteristic amount extraction section 6 acquires an event-related potential in response to the second sound being presented. Within the electroencephalogram data obtained at step S61, for example, a zone from −100 milliseconds to 400 milliseconds may be cut out, where the point in time of acquisition at step S62 is defined as 0 milliseconds, and used as the event-related potential.

At step S64, from the second sound presentation section 3b, the characteristic amount extraction section 6 acquires the attributes of the sound stimulation which has been presented as the second sound. The "attributes of the sound stimulation" include the tested ear, frequency, and sound pressure. An arithmetic mean is taken of the electroencephalogram data for each of these attributes, so as to be subjected to an uncomfortableness threshold value estimation process.

At step S65, the characteristic amount extraction section 6 accumulates the event-related potential having been cut-out, in association with the attributes acquired at step S64. Herein, the event-related potentials are stored in a storage device (not shown) internal to the characteristic amount extraction section 6 in association with the attributes. Alternatively, arithmetic mean waveform data may be stored, in which case the required storage capacity will be small.

With reference to FIG. 14, the processing by the characteristic amount extraction section 6 will be additionally described. Sound stimulations 41 are presented as paired stimulations 41a (and 41b) under certain attributes, e.g., right ear, 1000 Hz, 75 dB, and concurrently, an electroencephalogram 42 is being incessantly measured. Event-related potentials 43 are cut out in connection with the timing of presenting the second sound. An event-related potential 43a is acquired for the paired stimulations 41a. The event-related potential 43a and the attributes 44a of the corresponding sound stimulations are together accumulated in the characteristic amount accumulation 45. By repeating this, acquisition and accumulation of event-related potentials (43b, etc.) proceed.

Through such processes, an event-related potential in response to every second sound presented is stored in association with the attributes.

Next, the uncomfortableness threshold value estimation process shown at step S80 in FIG. 10 will be described in detail, with reference to FIGS. 15 and 16. This process is performed in the uncomfortableness threshold value estimation section 8. This is where an uncomfortableness threshold value of the user is estimated.

Figures 15, 16:
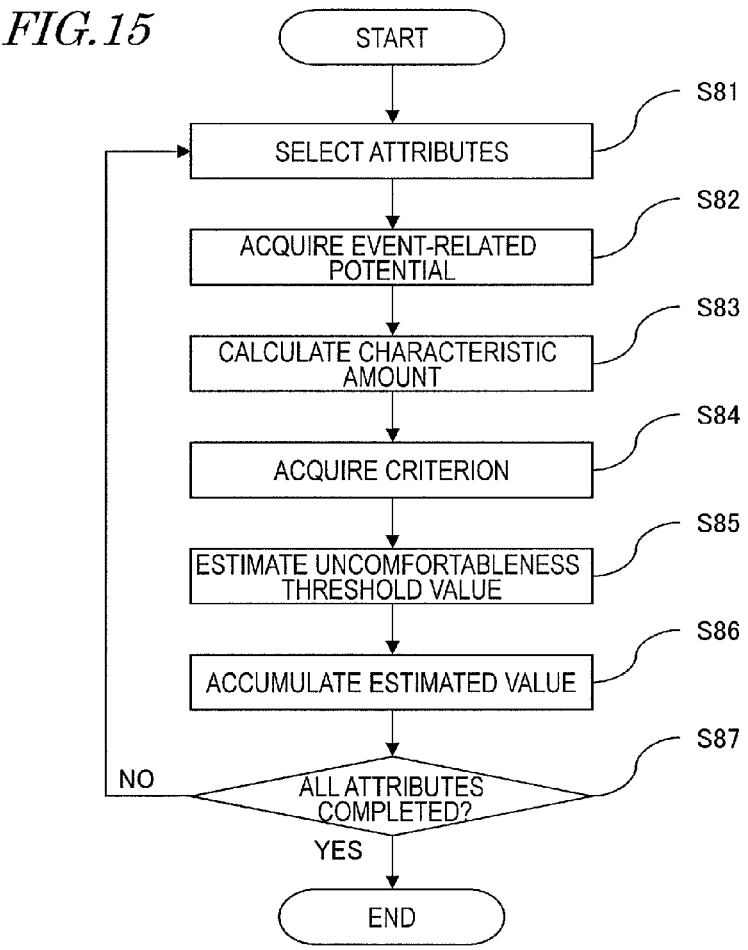
FIG. 15 is a flowchart of processing by an uncomfortableness threshold value estimation section 8.
FIG. 16 is a diagram showing an exemplary output format of uncomfortableness threshold values.

FIG. 15 shows a flowchart of processing by the uncomfortableness threshold value estimation section 8. FIG. 16 shows an exemplary output format of uncomfortableness threshold values.

At step S81, the uncomfortableness threshold value estimation section 8 selects attributes for an uncomfortableness threshold value to be estimated. The "attributes" as used herein are the combination of the tested ear 51 and the frequency 52 because, as shown in the example of FIG. 16, the uncomfortableness threshold value needs to be separately estimated for each of three frequencies and for either the right or left ear. In the present embodiment, an uncomfortableness threshold value estimation means making an estimation of the uncomfortableness threshold value 53 for each set of attributes.

At step S82, the uncomfortableness threshold value estimation section 8 acquires the event-related potentials 43 which have been accumulated corresponding to the attributes. The attributes herein are the tested ear 51 and the frequency 52, and event-related potentials associated with the respective presentation sound pressures are acquired.

At step S83, the uncomfortableness threshold value estimation section 8 calculates a characteristic amount concerning temporal changes in the frequency of event-related potential. For example, the characteristic amount is obtained by using a wavelet analysis or the like to calculate a frequency intensity in each time slot of the event-related potential at each of the sound pressures of 80 dB, 85 dB, and 90 dB, and then combining such coefficients into a vector.

The method of calculating the characteristic amount is further described. For each sound stimulation, the uncomfortableness threshold value estimation section 8 applies a continuous wavelet transform to an event-related potential waveform in the range from 0 ms to 300 ms, thereby calculating a wavelet coefficient for each time and each frequency. As a mother wavelet, the Mexican hat function ($\phi(t)=(1-t^2)\exp(-t^2/2)$) or the like may be used.

The waveform and wavelet coefficient of event-related potential are subjected to an arithmetic mean calculation for each condition, each individual person, either the right or left ear, and for frequency. Those trials which exhibit an amplitude in absolute value of 50 μV or more at any electrode are excluded from the total arithmetic mean and arithmetic mean, because they presumably are under the influence of noises, e.g., eye movements and blinks. Then, as a characteristic amount of event-related potential potentially serving as an index of uncomfortable sound pressure, an average value of the arithmetic mean wavelet coefficients in a frequency range from 5 Hz to 15 Hz is calculated in a time range of every 50 ms, and used as the characteristic amount. This characteristic amount may also be referred to as a wavelet characteristic amount.

At step S84, the uncomfortableness threshold value estimation section 8 acquires a criterion from the reference DB 7. Since the determination is based on a technique of estimating a UCL class based on a weighted sum of the respective characteristic amount values, the criterion is acquired in the form of a coefficient or the like for each characteristic amount value in the given instance.

At step S85, the uncomfortableness threshold value estimation section 8 makes a threshold determination based on the coefficient acquired at step S84 to estimate an uncomfortableness threshold value. Specifically, the uncomfortableness threshold value estimation section 8 performs a calculation based on any of various techniques of discriminant analysis, Bayesian estimation, and clustering, to derive an estimation of an uncomfortableness threshold value. The estimation is placed in a sound-pressure based format, as shown in FIG. 16, for example, where an uncomfortableness threshold value for the right ear at 1000 Hz reads 80 dB, and so on.

At step S86, the uncomfortableness threshold value estimation section 8 stores the uncomfortableness threshold value estimated at step S85. In a format such as that shown in FIG. 16, the uncomfortableness threshold value estimation result is calculated as a single value for the set of attributes selected at step S81, and stored.

At step S87, the uncomfortableness threshold value estimation section 8 determines whether the uncomfortableness threshold value estimation has been completed for all sets of attributes. If YES, the process is ended; if NO, control proceeds to step S81 to select a next set of attributes.

Through the above procedure, an uncomfortableness threshold value is estimated for every set of attributes, whereby results in a format as shown in FIG. 16 will finally be obtained.

FIG. 17A shows an exemplary data structure of the reference DB 7. As a really simple estimation criterion, an example will be illustrated where the wavelet coefficient from the second sound alone is used. Wavelet coefficients of the event-related potentials in response to the presentation sound pressures of 80 dB, 85 dB, and 90 dB are averaged, and from the relative size of this one resultant value, a UCL is estimated. FIG. 17A shows a table storing a relationship between the wavelet coefficient in response to the second sound and the UCL estimation value, which has been calculated from the data of an experiment conducted by the inventors (graph 22 in FIG. 4B(b))). Once a wavelet coefficient is calculated, the wavelet coefficient is looked up in this table, whereby a UCL estimation value is determined. For example, if the resultant wavelet coefficient is 5.0, the uncomfortableness threshold value estimation section 8 refers to the table to determine that the UCL estimation value is 90 dB.

Next, a method of generating the reference DB 7 will be described. The reference DB 7 is generated by acquiring data from a sufficient number of test subjects in advance. The number of test subjects from whom data is to be collected in advance should at least be 10 or more; in order to attain a sufficient precision, even more test subjects may be necessary. In the advance experiment, both an electroencephalogram and a subjective UCL are acquired from each test subject, and a criterion can be generated from correspondence between the electroencephalogram data and the subjective UCL values. For example, the graph of FIG. 4B(b) schematically illustrates correspondence between electroencephalogram characteristic amounts and subjective UCL values, which indicates a tendency that the wavelet coefficient decreases as the UCL estimation value decreases, and so on; thus, a threshold value is derivable from this graph, too.

In the example of FIG. 17A, this criterion can be generated by reading values on the vertical axis of graph 22 in FIG. 4B(b). When the distinction function becomes more complex, the threshold value needs to be determined by a technique such as machine learning. For example, discriminant analysis, Bayesian estimation, and the like, where calculations are performed after a coefficient is given to each characteristic amount, will be realized with the use of a more complex table and calculation scheme; however, an appropriate threshold value can be determined through calculation.

Thus, once the reference DB 7 is generated in advance, when a new user visits the shopfront, it is possible to estimate a UCL value from his or her electroencephalogram data alone, without asking for a subjective UCL.

The above description is directed to the case where a wavelet characteristic amount is used as a characteristic amount concerning temporal changes in the frequency of event-related potential. However, any other characteristic amount may be used so long as it contains information with which to estimate a subjective UCL value.

For example, the N1P2 amplitude described in the above section (2-2. Electroencephalogram measurement experiment) may be another example of a characteristic amount. This is believed to reflect an amount of change in the response to a sound.

Figure 17B:
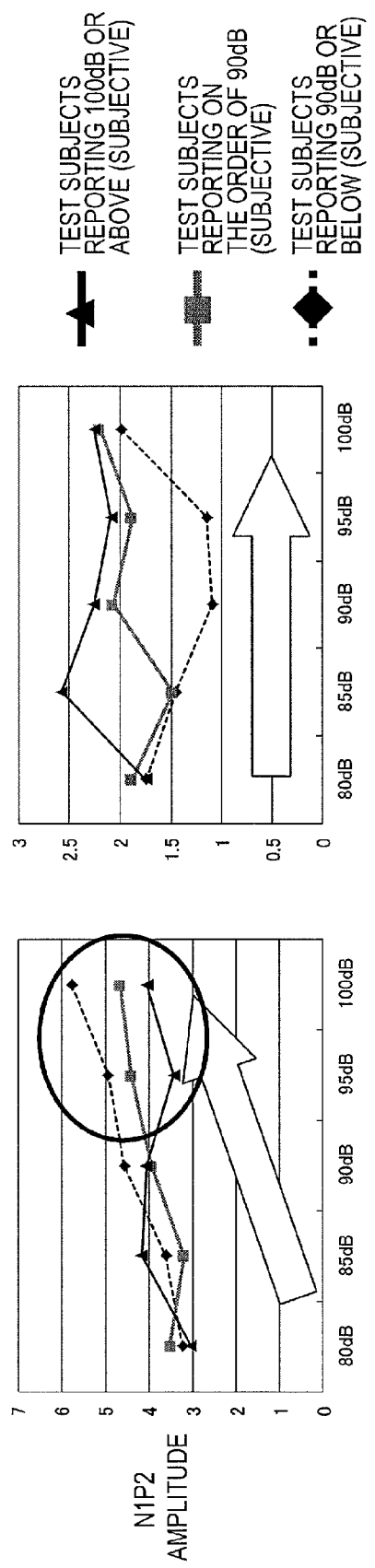
FIG. 17B is a diagram plotting values of an N1P2 characteristic amount in response to a first sound and a second sound, where experimental data obtained by the inventors is analyzed from another standpoint.

FIG. 17B is a diagram plotting values of an N1P2 characteristic amount in response to the first and second sounds, where experimental data obtained by the inventors is analyzed from another standpoint. This figure would correspond to FIG. 4B in the case of wavelet characteristic amounts. Each graph shows plotting similar to FIG. 4B, where test subjects are classified into three groups (subjective UCL of 100 dB or above, subjective UCL on the order of 90 dB, subjective UCL of 90 dB or below) based on the relative size of the UCL value through subjective reporting, and the characteristic amounts within each group are averaged.

As will be understood from FIG. 17B, particularly in the ERP in response to the second sound, the relationship between subjective UCL levels is conserved in the relationship between N1P2 amplitude levels. Thus, it is indicated that subjective UCL values are estimatable by setting an appropriate threshold value.

FIG. 17C shows an example of the reference DB 7 in the case where N1P2 amplitude is used as a characteristic amount. Herein, as a really simple estimation criterion, an example will be illustrated where the N1P2 amplitude 56 with respect to the second sound alone is used. N1P2 amplitudes of the event-related potentials in response to the presentation sound pressures of 80 dB, 85 dB, and 90 dB are averaged, and from the relative size of this resultant average value, a UCL estimation value 57 is obtained. Thus, a UCL value is estimatable from the relative size of the average amplitude change. For example, if the N1P2 amplitude for the second sound is 1.8, then the UCL value output will be 95 dB.

Furthermore, characteristic amounts other than wavelet coefficients or N1P2 amplitude may also be used. A characteristic feature of an event-related potential manifests itself in the waveform shape, and thus is describable in terms of latency (i.e., elapsed time from the timing of presenting a stimulation) and amplitude of a peak that appears. Any form of description of such a characteristic feature that is made in terms of time, frequency, or shape would be available as a characteristic feature for distinction. In the present specification, the wavelet coefficient is an example of information that is indicative of temporal change in the frequency of an event-related potential. Moreover, a machine learning technique such as discriminant analysis or Bayesian estimation may be employed, to which conceivable characteristic amounts may be supplied in vectorial form, whereby the respective parameters will be appropriately weighted. This will eliminate the need to previously narrow down to any one characteristic amount.

The present embodiment has illustrated an example where a UCL value is estimated with respect to pure tones. However, the sounds to be presented by the presentation sound control section 3 are not limited to pure tones, but may instead be speech sounds. In the case of presenting speech sounds, a plurality of frequency components will be mixedly present, which makes frequency-by-frequency assessment impossible; thus, an assessment for either the right or left ear is to be made. The presentation sound control section 3 may previously retain the speech sounds to be presented. In that case, the sound pressure range or average sound pressure for speech sounds is adjustable in advance.

FIG. 17D shows an exemplary output format of uncomfortableness threshold values in the case where speech sounds are employed. A relationship between the tested ear 58 and the uncomfortableness threshold value 59 is defined. In the case where an uncomfortableness threshold value 59 has been successfully output for each of the right and left ears, that uncomfortableness threshold value is applicable to the overall gain adjustment (sound volume adjustment) for the respective right or left ear in fitting a hearing aid. In the sound volume adjustment or the like of a television set, a music player, etc., for example, if the uncomfortableness threshold value varies from right to left, better hearing can be provided by modifying the right and left gains.

Discriminant analysis, Bayesian estimation, and the like, where calculations are performed after a coefficient is given to each characteristic amount, will be realized with the use of a more complex table and calculation scheme; however, a distinction criterion can be determined by finding an appropriate value through learning or the like, from pairs of electroencephalogram data and UCL estimation values obtained from experimentation.

Note that this UCL evaluation result is to be used as a piece of information for setting a maximum output value for a hearing aid when "fitting" the hearing aid.

Figure 18:
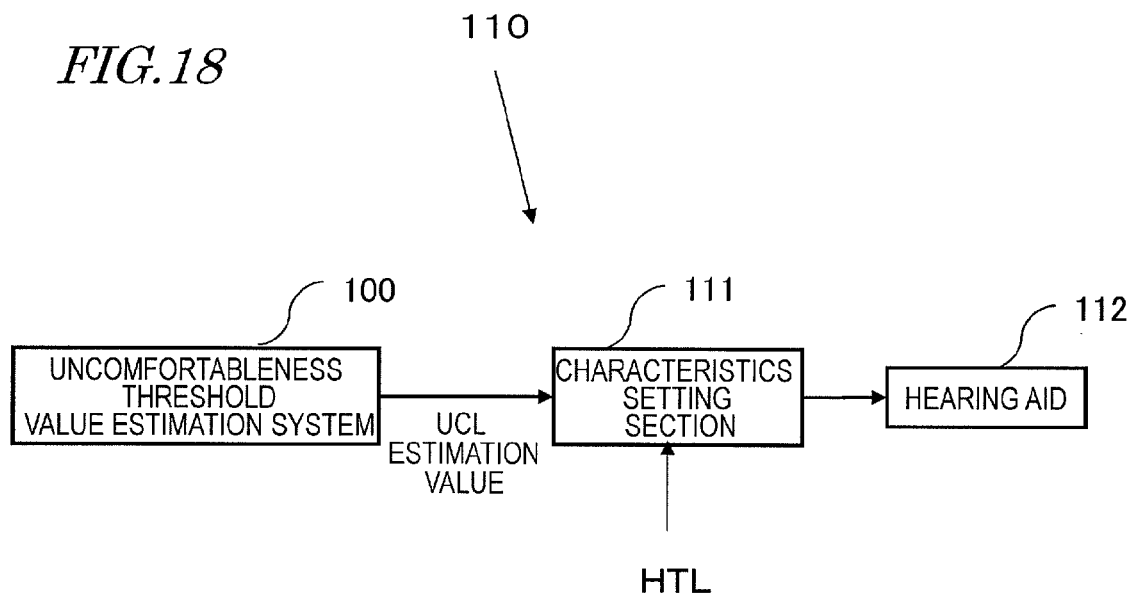
FIG. 18 is a block diagram showing the construction of a hearing aid adjustment system 110.

For example, FIG. 18 shows the construction of a hearing aid adjustment system 110. The hearing aid adjustment system 110 includes the uncomfortableness threshold value estimation system 100 shown in FIG. 7, as well as a characteristics setting section 111 and a hearing aid 112. Note that the uncomfortableness threshold value estimation system 100 is an example. Instead of the uncomfortableness threshold value estimation system 100, a hearing aid adjustment system may be constructed by using an uncomfortableness threshold value estimation system 101 shown in FIG. 19.

The characteristics setting section 111 receives uncomfortableness threshold values that have been estimated by the uncomfortableness threshold value estimation system 100, and hearing threshold levels HTL each indicating a minimum sound pressure of a pure tone that the user 1 is able to hear. The pure tone frequencies may be 250 Hz, 500 Hz, 1000 Hz, 2000 Hz, and 4000 Hz, for example. A hearing threshold level HTL is defined for each frequency. The hearing threshold levels HTL may be sent from a device for measuring the hearing threshold level (audiometer; not shown) in a wired or wireless manner, or via a storage medium or the like, for example. Then, the characteristics setting section 111 sets each uncomfortableness threshold value to the hearing aid 112 as a maximum output value, and sets each hearing threshold level HTL as a minimum output value to the hearing aid 112.

Figure 19:
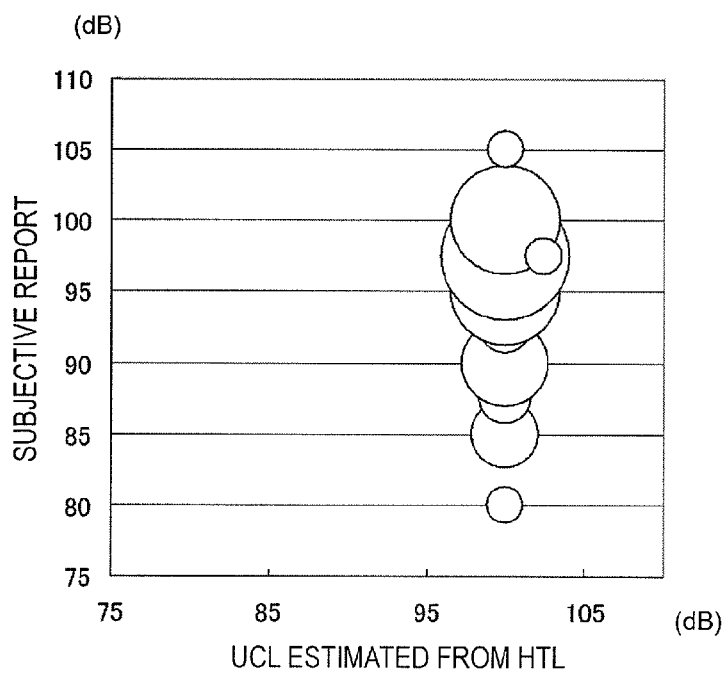
FIG. 19 is a diagram showing individual differences in UCL through subjective reporting, based on an MCL mirror method.

Conventionally, a predetermined value which is determined in accordance with the HTL is set as the maximum output value. However, according to the conventional technique (MCL mirror method), even those test subjects whose uncomfortableness threshold values are invariably at 100 dB have been found to permit individual differences in subjectively-reported UCL. FIG. 19 is a diagram showing individual differences in UCL through subjective reporting, based on an MCL mirror method. The horizontal axis represents UCL as estimated by the MCL mirror method. Since people with normal hearing are being tested, there is little variation in HTL, so that the estimated UCL values are basically the same. However, as is indicated by the vertical axis of FIG. 19 representing UCL values obtained through subjective reporting, the conventional method cannot account for individual differences in UCL. If an output range of the hearing aid can be correctly set based on an estimated UCL, the time required for the fitting of the hearing aid will become shorter than conventional. In setting an initial fitting value for the hearing aid, too, it will also allow a more appropriate initial value to be set than in the conventional method.

With this construction, based on electroencephalogram, a UCL value which a test subject is expected to subjectively report can be estimated, without actually causing the test subject to hear any overbearing sounds. This can be utilized as useful information for hearing aid fitting.

Hereinafter, a variant of the above embodiment will be described. Specifically, an example will be described where, additionally to the above embodiment, an event-related potential occurring in response to the first sound that is presented under the control of the first sound presentation section is also utilized for uncomfortableness threshold value estimation. The use of more information can make for improved precision.

Figure 20:
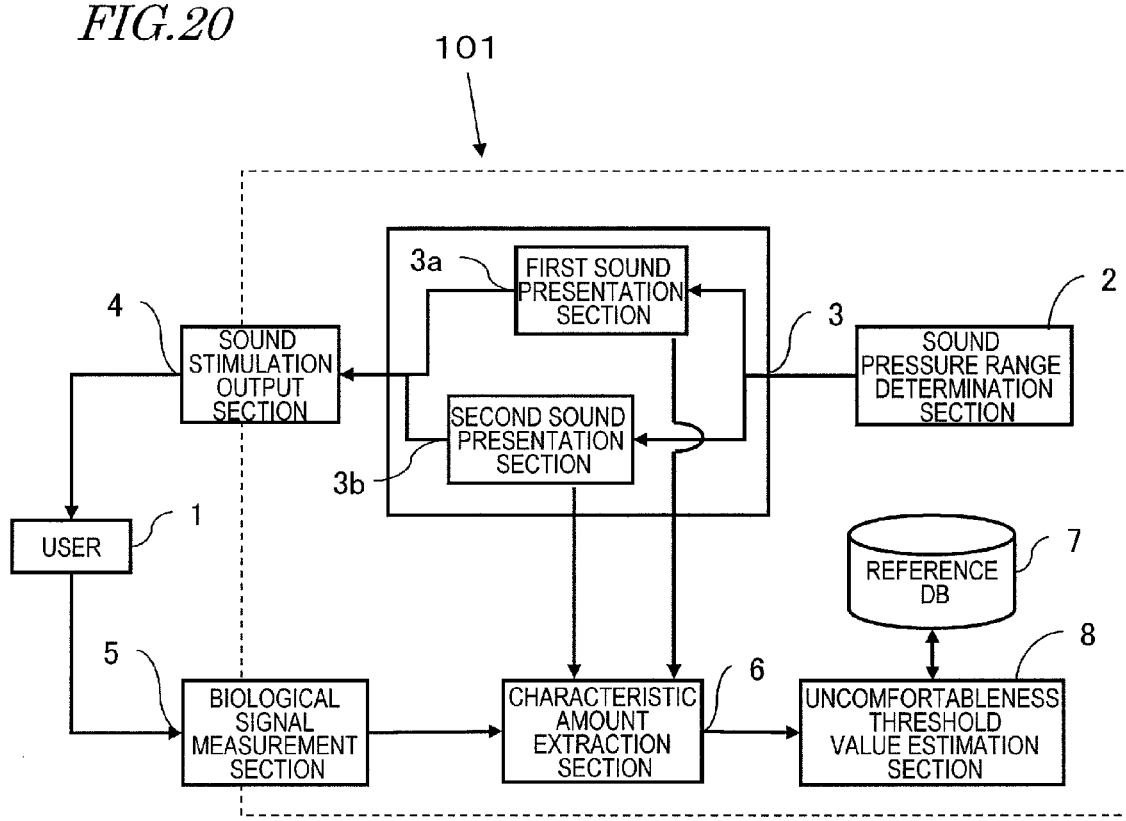
FIG. 20 is a block diagram showing the construction of an uncomfortableness threshold value estimation system 101 according to a variant of the illustrative embodiment of the present invention.

FIG. 20 shows the construction of an uncomfortableness threshold value estimation system 101 according to a variant of the illustrative embodiment of the present disclosure. The uncomfortableness threshold value estimation system 101 is obtained by modifying the construction of the uncomfortableness threshold value estimation system 100 (FIG. 7). In the construction of the uncomfortableness threshold value estimation system 101, any constituent element which is identical to that in the uncomfortableness threshold value estimation system 100 (FIG. 7) will be denoted by the same reference numeral, and the description thereof will be omitted. The uncomfortableness threshold value estimation system 101 differs from the uncomfortableness threshold value estimation system 100 in that there is extra connection from the first sound presentation section 3a to the characteristic amount extraction section 6. Therefore, the detailed operation of the presentation sound control section 3 and the characteristic amount extraction section 6 will be mainly described below.

Figure 21:
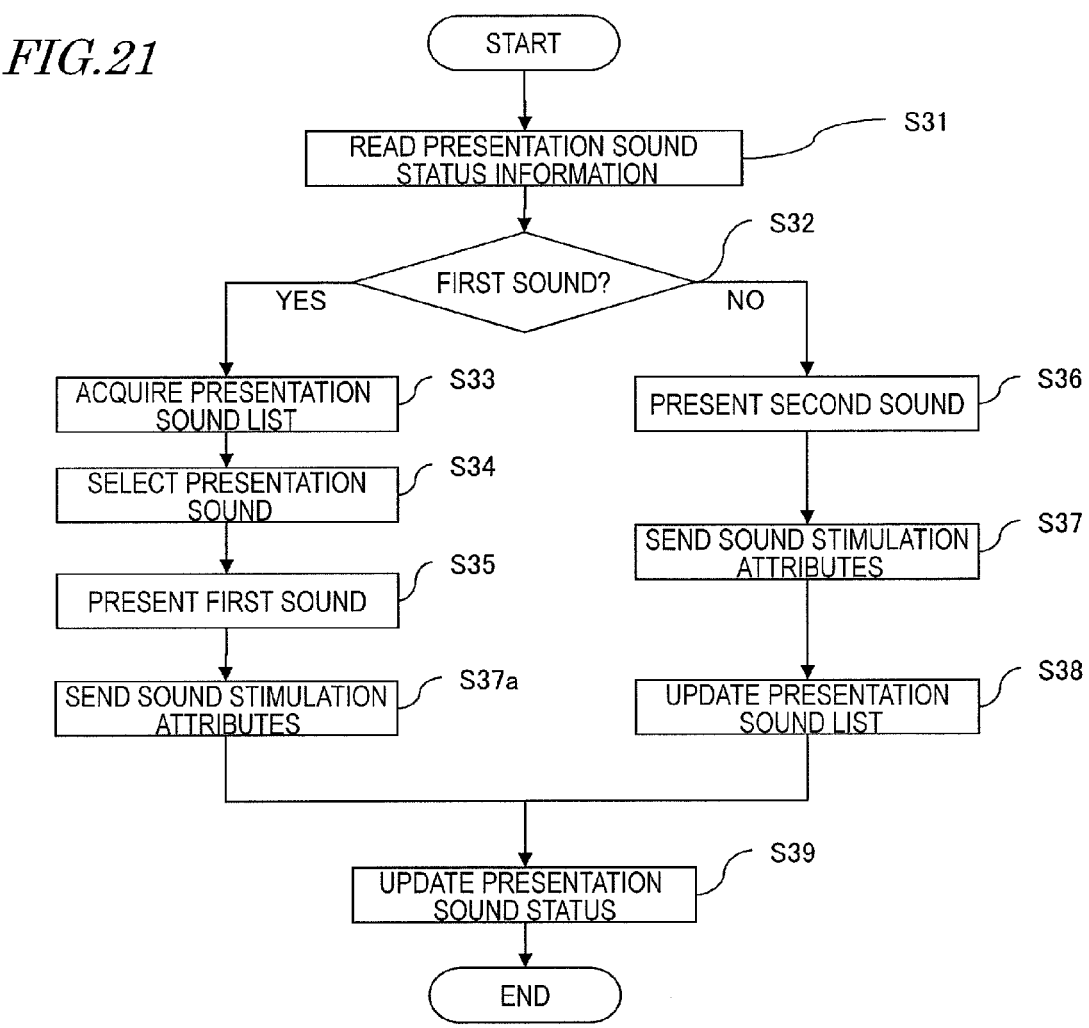
FIG. 21 is a flowchart showing a processing procedure by a variant of the presentation sound control section 3.

FIG. 21 shows a flow of control of the presentation sound control section 3 according to this variant. Since basically similar processes to those in FIG. 11 are being performed, like processes are denoted by like reference numerals, with their descriptions omitted. The difference from FIG. 11 is a new step S37a being added after the first sound presentation at step S35. In step S37a, the sound stimulation attributes of the first sound are sent to the characteristic amount extraction section 6. As used herein, the sound stimulation attributes are information concerning the tested ear, the frequency, and concerning which sound pressure is presented at which timing.

The operation of the characteristic amount extraction section 6 also slightly differs from that in Embodiment 1. The basic processing flow is similar to that of FIG. 13, except that the timing of accumulation comes not only after second sound presentation, but also after first sound presentation.

Figure 22:
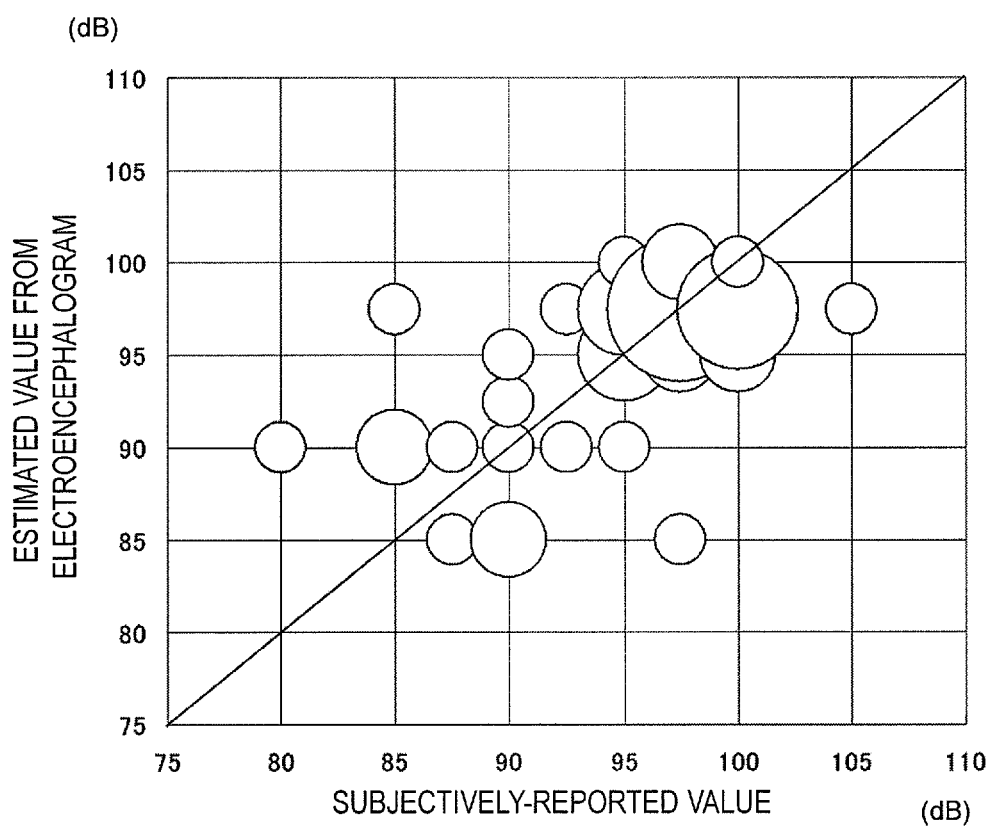
FIG. 22 is a diagram showing instances of estimation results in the case of using both of event-related potentials obtained after sound stimulations of a first sound and a second sound are presented.

FIG. 22 shows instances of estimation results in the case of using both of event-related potentials obtained after sound stimulations of the first and second sounds are presented. From among various characteristic amount combinations of event-related potentials after presenting the first and second sounds, the inventors have extracted those instances which resulted in a high precision, thus arriving at FIG. 22. Three presentation sound pressures of 80 dB, 85 dB, and 90 dB were used. As for the characteristic amounts, the UCL estimation was made by using both of: an N1P2 amplitude ratio between the event-related potentials in response to the first and second sounds; and a wavelet coefficient of the event-related potential in response to the second sound. In FIG. 22, the horizontal axis represents subjectively-reported values, and the vertical axis represents estimated values based on the electroencephalogram, where the diameter of each plotted circle is in proportion to the number of instances in question. If all results are on a straight line, it may be said that the UCL estimation values all correctly corresponded to the subjectively-reported values. The fluctuations from the subjective report were 3.75±3.89 dB. A mean value of errors from the subjective reports was 3.15±3.05 dB. This example can be deemed to have produced a precision which is improved over that of Embodiment 1, i.e., 3.87±3.09 dB, where only the response to the second sound was used.

Note that this illustrates only one instance for demonstrating an improvement in precision. Various calculation methods and combinations of characteristic amounts would be possible, and characteristic amounts and criteria that may lead to even greater improvements in precision might be broadly sought.

Through such processes, in addition to an event-related potential in response to the second sound presentation, information of an event-related potential in response to the first sound presentation is also employed, whereby precision improvements and a reduction in the number of presentations may become possible. By utilizing this variant construction, it would be possible to realize a hearing aid adjustment system having a similar construction to the construction shown in FIG. 18.

A brief discussion of the reason for precision improvements is provided. As far as the first sound is concerned, a response to the loudness of the presented sound is known to appear as an N1 component which is centered around 100 milliseconds after the sound presentation. The aforementioned improvements in precision indicate the possibility that this may also contain some information that is related to UCL.

Note that, since the event-related potential in response to the first sound presentation alone cannot provide an adequate precision in UCL estimation, the event-related potential in response to the second sound is considered essential to be employed.

With an uncomfortableness threshold value estimation system according to an illustrative embodiment of the present disclosure, an uncomfortableness threshold value of a user can be estimated without presenting any overbearing sound stimulations, which will be useful for the hearing aid adjustment at a hearing aid shop, in a household, and so on. For a person with normal hearing, too, previously estimating an uncomfortableness threshold value will have its applications in setting a maximum sound volume for audio devices such as a television set, a stereo set, and the like.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortableness threshold value estimation system comprising:
   one or more memories; and
   circuitry which in operation is configured to:
   present to a user a first sound, and to present to the user a second sound after lapse of a first predetermined time from a point of presenting the first sound, the first sound having a sound pressure within a predetermined sound pressure range, and the second sound having a same sound pressure as that of the first sound;
   measure an electroencephalogram signal of the user;
   extract, from an electroencephalogram signal which is measured within a second predetermined time from a point of presenting the second sound, and which is evoked by the second sound, a characteristic amount of an event-related potential of the electroencephalogram signal; and
   estimate, by referring to a predetermined relationship between characteristic amount values of event-related potential and uncomfortableness threshold values, an uncomfortableness threshold value corresponding to the extracted characteristic amount of the event-related potential, the uncomfortableness threshold values not being originated with event-related potential values.

2. The uncomfortableness threshold value estimation system of claim 1, wherein the circuitry further is configured to determine the predetermined sound pressure range according to a predetermined criterion, and to control the first sound and the second sound so as to be presented from the output section at a sound pressure which is equal to or less than an upper limit of the sound pressure range.

3. The uncomfortableness threshold value estimation system of claim 2, wherein the circuitry further is configured to output the first sound and the second sound at a predetermined frequency and sound pressure.

4. The uncomfortableness threshold value estimation system of claim 2, wherein the circuitry further is configured to present a speech sound in a predetermined sound pressure range as the first sound and the second sound.

5. The uncomfortableness threshold value estimation system of claim 2, wherein the circuitry further is configured to present the second sound after 100 milliseconds or more have elapsed from the point of presenting the first sound.

6. The uncomfortableness threshold value estimation system of claim 2, wherein,
the circuitry further is configured to output at least two pairs of sound stimulations, where each pair of sound stimulations is defined by a first sound and a second sound; and
the circuitry further in configured to change the sound pressure from sound stimulation to sound stimulation.

7. The uncomfortableness threshold value estimation system of claim 2, wherein,
the circuitry further is configured to output a first pair of sound stimulations and a second pair of sound stimulations, where each pair of sound stimulations is defined by a first sound and a second sound; and
the circuitry further is configured to control the sound stimulations so that the first pair of sound stimulations is presented and then the second pair of sound stimulations is presented within a range of 1000 ms±200 ms therefrom.

8. The uncomfortableness threshold value estimation system of claim 1, wherein,
the extracts circuitry further is configured to extract a wavelet coefficient concerning time and frequency as the characteristic amount, by applying a wavelet transform to the electroencephalogram signal which is measured within the second predetermined time from the point of presenting the second sound.

9. The uncomfortableness threshold value estimation system of claim 8, wherein, by referring to a reference database defining a relationship between wavelet coefficients and uncomfortableness threshold values, the circuitry further is configured to estimate an uncomfortableness threshold value corresponding to the wavelet coefficient obtained as the characteristic amount.

10. The uncomfortableness threshold value estimation system of claim 1, wherein,
the second predetermined time is a period in which an N1 component and a P2 component of the event-related potential in response to the second sound are observable; and
the circuitry further is configured to extract an N1P2 amplitude as the characteristic amount, the N1P2 amplitude being an absolute value of a difference between a peak potential of the N1 component and a peak potential of the P2 component.

11. The uncomfortableness threshold value estimation system of claim 10, wherein, by referring to a reference database defining a relationship between N1P2 amplitudes and uncomfortableness threshold values, the circuitry further is configured to estimate an uncomfortableness threshold value corresponding to the N1P2 amplitude obtained as the characteristic amount.

12. A hearing aid adjustment system comprising:
a hearing aid;
the uncomfortableness threshold value estimation system of claim 1; and
the circuitry further is configured to receive the uncomfortableness threshold value estimated by the uncomfortableness threshold value estimation system and setting the uncomfortableness threshold value to the hearing aid as a maximum output value.

13. An uncomfortableness threshold value processing circuit which receives an electroencephalogram signal of a user measured by a biological signal measurement circuitry, and causes an output circuitry to present a sound stimulation,
the uncomfortableness threshold value processing circuit comprising: one or more memories; and circuitry which in operation is configured to:
cause the output circuitry to present a first sound, and to present a second sound after lapse of a first predetermined time from a point of presenting the first sound, the first sound having a sound pressure within a predetermined sound pressure range, and the second sound having the sound pressure;
extract, from an electroencephalogram signal which is measured within a second predetermined time from a point of presenting the second sound, and which is evoked by the second sound, a characteristic amount of an event-related potential of the electroencephalogram signal; and estimate, by referring to a predetermined relationship between characteristic amount values of event-related potential and uncomfortableness threshold values, an uncomfortableness threshold value corresponding to the extracted characteristic amount of the event-related potential, the uncomfortableness threshold values not being originated with event-related potential values.

14. An uncomfortableness threshold value estimation method, comprising the steps of:
presenting to a user a first sound and presenting to the user a second sound after lapse of a first predetermined time from a point of presenting the first sound, the first sound having a sound pressure within a predetermined sound pressure range,
and the second sound having a same sound pressure as that of the first sound; measuring an electroencephalogram signal of the user; from an electroencephalogram signal which is measured within a second predetermined time from a point of presenting the second sound, extracting a characteristic amount of an event-related potential of the electroencephalogram signal, and which is evoked by the second sound; and
by referring to a predetermined relationship between characteristic amount values of event-related potential and uncomfortableness threshold values, estimating an uncomfortableness threshold value corresponding to the extracted characteristic amount of the event-related potential, the uncomfortableness threshold values not being originated with event-related potential values.

15. A non-transitory computer-readable medium storing a computer program to be executed by a computer provided in an uncomfortableness threshold value processing circuit of an uncomfortableness threshold value estimation system, the computer program causing the computer to execute the steps of: presenting to a user a first sound and presenting to the user a second sound after lapse of a first predetermined time from a point of presenting the first sound, the first sound having a sound pressure within a predetermined sound pressure range, and the second sound having a same sound pressure as that of the first sound; acquiring an electroencephalogram signal of the user; from an electroencephalogram signal which is measured within a second predetermined time from a point of presenting the second sound, extracting a characteristic amount of an event-related potential of the electroencephalogram signal, said extraction evoked by the second sound; and by referring to a predetermined relationship between characteristic amount values of event-related potential and uncomfortableness threshold values, estimating an uncomfortableness threshold value corresponding to the extracted characteristic amount of the event-related potential, the uncomfortableness threshold values not being originated with event-related potential values.

16. An uncomfortableness threshold value estimation system comprising:

one or more memories; and circuitry which in operation is configured to:

determine a sound pressure range in which to present sounds to a user;

determine first and second sounds to be presented at a predetermined time interval, the first and second sounds being of a same sound pressure and frequency, the sound pressure being in the sound pressure range;

output the first and second sounds as sound stimulations;

measure an electroencephalogram of the user;

acquire, from the measured electroencephalogram, an event-related potential based on a timing of outputting the second sound as a starting point, and to accumulate the event-related potential together with attributes of the second sound presented, the attributes being the sound pressure, the frequency, and a tested ear, which is evoked by the second sound;

the one or more memories storing a reference database retaining a criterion for estimating an uncomfortableness threshold value from a characteristic amount of the event-related potential; and an uncomfortableness threshold value estimation section the circuitry further is configured to process data accumulated in the event related potential acquisition/accumulation section in accordance with the criterion retained in the reference database, and to estimate an uncomfortableness threshold value, the uncomfortableness threshold value exceeding the sound pressure range determined by the sound pressure range determination section circuitry, and the uncomfortableness threshold values not being originated with event-related potential values.

* * * * *